(12) United States Patent
Dubois et al.

(10) Patent No.: US 8,354,425 B2
(45) Date of Patent: Jan. 15, 2013

(54) AZABICYCLIC CARBOXAMIDE DERIVATIVES, PREPARATION THEREOF AND THERAPEUTIC USE THEREOF

(75) Inventors: Laurent Dubois, Paris (FR); Yannick Evanno, Paris (FR); David Machnik, Paris (FR); André Malanda, Paris (FR)

(73) Assignee: Sanofi, Paris (FR)

( * ) Notice: Subject to any disclaimer, the term of this patent is extended or adjusted under 35 U.S.C. 154(b) by 163 days.

(21) Appl. No.: 12/840,659

(22) Filed: Jul. 21, 2010

(65) Prior Publication Data
US 2011/0009364 A1    Jan. 13, 2011

Related U.S. Application Data

(63) Continuation of application No. PCT/FR2009/000052, filed on Jan. 20, 2009.

(30) Foreign Application Priority Data

Jan. 22, 2008    (FR) ..................... 08 00308

(51) Int. Cl.
*A61K 31/4353* (2006.01)
*C07D 471/02* (2006.01)
(52) U.S. Cl. ......... 514/300; 546/112; 546/113; 514/299
(58) Field of Classification Search .......... 546/112, 546/113; 514/299, 300
See application file for complete search history.

(56) References Cited

U.S. PATENT DOCUMENTS

| | | | |
|---|---|---|---|
| 7,384,969 B2 | 6/2008 | Dubois et al. | |
| 7,407,950 B2 | 8/2008 | Dubois et al. | |
| 7,557,134 B2 * | 7/2009 | Dubois et al. | 514/414 |
| 7,745,467 B2 | 6/2010 | Dubois et al. | |
| 7,763,636 B2 | 7/2010 | Dubois et al. | |
| 7,786,104 B2 * | 8/2010 | DuBois et al. | 514/210.2 |
| 7,868,024 B2 * | 1/2011 | Dubois et al. | 514/339 |
| 8,044,066 B2 * | 10/2011 | Dubois et al. | 514/300 |
| 8,153,650 B2 * | 4/2012 | Dubois et al. | 514/299 |
| 2005/0256125 A1 | 11/2005 | Kath et al. | |
| 2009/0042873 A1 | 2/2009 | Dubois et al. | |
| 2009/0298865 A1 | 12/2009 | Dubois et al. | |
| 2011/0009365 A1 | 1/2011 | Dubois et al. | |
| 2011/0009400 A1 | 1/2011 | Dubois et al. | |
| 2011/0009444 A1 | 1/2011 | Dubois et al. | |

FOREIGN PATENT DOCUMENTS

| | | |
|---|---|---|
| FR | 2 677 358 | 12/1992 |
| JP | 2001 151771 | 6/2001 |
| WO | WO 03/068749 | 8/2003 |
| WO | WO 2005/032493 | 4/2005 |
| WO | WO 2005/072681 | 8/2005 |
| WO | WO 2005/080328 | 9/2005 |
| WO | WO 2006/024776 | 3/2006 |
| WO | WO 2006/040520 | 4/2006 |
| WO | WO 2006/072736 | 7/2006 |
| WO | WO 2007/010138 | 1/2007 |
| WO | WO 2007/010144 A1 | 1/2007 |
| WO | WO 2007/088277 | 8/2007 |
| WO | WO 2008/107543 | 9/2008 |

OTHER PUBLICATIONS

International Search Report for WO2009/112678 dated Sep. 17, 2009.
Ye et al, A Novel Method for the Synthesis of Regiospecifically Sulfonated Porphyrin Monomers and Dimers, Tetrahedron, 2003 (59) pp. 3593-3601.
Abramovitch et al. Microwave-Assisted Alkylations of Activated Methylene Groups, Synthetic Communications, 1995 (25)1 pp. 1-8.
Antilla et al, The Copper-Catalyzed N-Arylation of Indoles, J. Am. Chem. Soc., 2002 (124) pp. 11684-11688.
Cabiddu et al, Metaliation reactions. Part 35: A change of the regiochemistry in the metallation of (alkylthio) erenes, Tetrahedron, 2004 (60) pp. 3915-3920.
Davies et al, Preparation of Tricarbonyl(n6-pyridine)chromium(0) Complexes, J. Chem. Soc. Perkin Trans 1, 1991 pp. 501-507.
Frissen et al, Novel Intramolecular Diets—Alder Reactions of Pyrimidines. Synthesis of Heterocyclic Annelated Pyridines, Tetrahedron Lett., 1987 (28)14 pp. 1589-1592.
Furstner et al, Iron-Catalyzed Cross-Coupling Reactions, J. Am Chem Soc., 2002 (124) pp. 13856-13853.
Goossen et al, A Mild and Efficient Protocol for the Catalytic Silylation of Aryl Bromides, Synlett, 2000 (12) pp. 1801-1803.
Guillard et al, Synthesis of New Melatonin Analogues from Dimers of Azaindole and Indole by Use of Suzuki Homocoupling, Heterocycles, 2003 (60)4 pp. 865-877.
Henn et al, Formation of Indoles, Isoquinolines, and Other Fused Pyridines from Azidoacrylates, J. Chem. Soc. Perkin Trans. 1, 1984 pp. 2189-2196.
Hoesl et al, Synthesis of Sterically Demanding Demanding 3-Silylpyridines and Their Use in Asymmetric Synthesis with Chiral N-Acyliminium Ions, Heterocycles, 2002 (58) pp. 383-392.
Ishimaru et al, Diastereoselective Synthesis of trans-N-Benzyl-2-(2-methylphenyl)-6-phenyl-4-piperidione, Heterocycles, 2001 (55) 8 pp. 1591-1598.
Kim et al, Synthese d'acetyl-6 et benzyl-6 indoles, J. Heterocyclic Chem., 1981 (18) pp. 1365-1371.

(Continued)

*Primary Examiner* — Golam M M Shameem
(74) *Attorney, Agent, or Firm* — Kelly L. Bender

(57) ABSTRACT

The disclosure relates to compounds of formula (I):

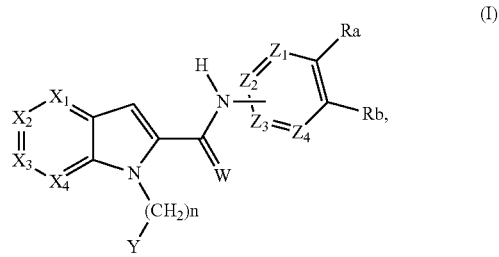

wherein $X_1$, $X_2$, $X_3$, $X_4$, $Z_1$, $Z_2$, $Z_3$, $Z_4$, Ra, Rb, n, Y, and W are as defined in the disclosure, or a salt thereof, or a hydrate or solvate thereof, and to processes for the preparation of these compounds and the therapeutic use thereof.

14 Claims, No Drawings

OTHER PUBLICATIONS

Klapars et al, A General and Efficient Copper Catalyst for the Amidation of Aryl Halides and the N-Arylation of Nitrogen Heterocycles, J. Am. Chem. Soc., 2001 (123) pp. 7727-7729.

Knittel et al, Verbesserte Synthese Von a-Azidozimtsaure-Estem und 2H-Azirinen, Synthesis, 1985 (2) pp. 186-188.

Marsais et al, Synthesis and Structural Study of 2,5-Dihydropyridines, Competitve Metalation of 2-Fluoropyridine, J. Org. Chem., 1981 (46) pp. 4494-4497.

Mitsunobu, The Use of Diethyl Azodicarboxylate and Triphenylphosphine in Synthesis and Transformation of Natural Products, Synthesis, 1981 pp. 1-28.

Molina et al, Carbodiimide-Mediated Preparation of the Tricyclic Pyrido[3',2':4,5]pyrrolo 1,2-c]pyrimidine Ring System and Its Application to the Synthesis of the Potent Antitumoral Marine Alkaloid Variolin B and Analog, J. Org. Chem., 2003 (68) pp. 489-499.

Pearson et al, A Practical, Efficient Synthesis of 5-Amino-7-azaindole, Synthesis, 2005 (15) pp. 2503-2506.

Pierrat et al. Unusual t-BuLi Induced Ortholithiation versus Halogen-Lithium Exchange in Bromopyridines: Two Alternative Strategies for Functionalization, SynLett, 2004 (13) pp. 2319-2322.

Roy et al, The Hemetsberger-Knittel Synthesis of Substituted 5-, 6-, and 7-Azaindoles, Synthesis, 2005 (16) pp. 2751-2757.

Sadighi et al, Palladium-Catalyzed Synthesis of Monodisperse, Controlled-Length, and Functionalized Oligoanilines, J. Am. Chem. Soc., 1998 (120) pp. 4960-4976.

Sawyer et al, Carbocyclic[g]indole Inhibitors of Human Nonpancreatic s-PLA2, J. Med. Chem., 2005 (48) pp. 893-896.

Shippey et al, Trimethylsilyi Anoins, Direct Synthesis of Trimethylsilylbenzenes, J. Org. Chem., 1977 (42) 15 pp. 2654-2655.

Stokes et al, Intramolecular C-H Amination Reactions: Exploitation of the Rh2(II)-Catalyzed Decomposition of Azidoacrylates, J. Am. Chem. Soc., 2007 (129) pp. 7500-7501.

Storz et al, The First Practical and Efficient One-Pot Synthesis of 6-Substituted 7-Azaindoles via a Reissert-Henze Reaction, Synthesis, 2008 (2) pp. 201-214.

Trecourt et al, First Syntheses of Caerulomycin E and Collismycins A and C. A New Synthesis of Caerulomycin A, J. Org. Chem., 1998 (63) pp. 2892-2897.

Trecourt et al, New Syntheses of Substituted Pyridines via Bromine-Magnesium Exchange, Tetrahedron, 2000 (56) pp. 1349-1360.

Vital et al, An Intramolecular Heck Reaction that Prefers a 5-endo- to a 6-exo-trig Cyclization Pathway, SynLett, 2006 (18) pp. 3140-3144.

Williams et al, 5-Chloro-3-(Phenylsulfonyl)Indole-2-Carboxamide: A Novel, Non-Nucleoside Inhibitor of HIV-1 Reverse Transcriptase, J. Med. Chem., 1993 (36) pp. 1291-1294.

Kolasa, T., et al., Synthesis of Indolylalkoxyiminoalkylcarboxylates as Leukotriene Biosynthesis Inhibitors, Bioorganic & Medicinal Chemistry, vol. 5, No. 3, pp. 507-514, (1997).

* cited by examiner

AZABICYCLIC CARBOXAMIDE DERIVATIVES, PREPARATION THEREOF AND THERAPEUTIC USE THEREOF

Documents WO2006/024776, WO2006/072736, WO2007/010144 and WO2007/010138 describe bicyclic carboxamide derivatives with in vitro and in vivo antagonist or agonist activity on receptors of TRPV1 (or VR1) type.

There is still a need to find novel ligands for receptors of TRPV 1 type, which are improved in terms of functional activity, metabolic profile and/or safety profile.

The present invention satisfies this need by providing azabicyclic carboxamide derivatives that have in vitro and in vivo antagonist or agonist activity on receptors of TRPV1 (or VR1) type.

A first subject of the invention concerns the compounds corresponding to the general formula (I) hereinbelow.

Another subject of the invention concerns processes for preparing the compounds of general formula (I).

Another subject of the invention concerns the use of the compounds of general formula (I) especially in medicaments or in pharmaceutical compositions.

The compounds of the invention correspond to the general formula (I):

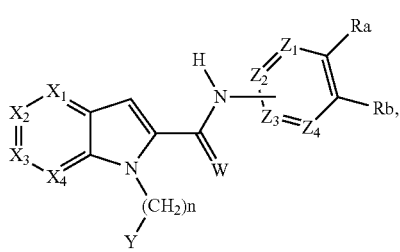

in which:
$X_1$, $X_2$, $X_3$ and $X_4$ represent, independently of each other, a nitrogen atom or a group C—$R_1$;
it being understood that when one from among $X_1$, $X_2$, $X_3$ and $X_4$ represents a nitrogen atom, the others correspond to a group C—$R_1$;
$Z_1$, $Z_2$, $Z_3$ and $Z_4$ represent, independently of each other, a nitrogen atom, a carbon atom or a group C—$R_2$, at least one from among $Z_1$, $Z_2$, $Z_3$ and $Z_4$ corresponding to a nitrogen atom and one from among $Z_1$, $Z_2$, $Z_3$ and $Z_4$, corresponding to a carbon atom, being bonded to the nitrogen atom of the amide or of the thioamide of formula (I);
Ra and Rb form, together with the carbon atoms that bear them, a 5-membered ring, this ring comprising a nitrogen atom and carbon atoms, this ring being partially saturated or unsaturated and being optionally substituted with one or more substituents $R_3$;
W represents an oxygen or sulfur atom;
n is equal to 0, 1, 2 or 3;
Y represents an aryl or a heteroaryl optionally substituted with one or more groups chosen from a halogen atom, a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkyloxy, $C_3$-$C_7$-cycloalkyl-$C_1$-$C_6$-alkylene-O—, $C_1$-$C_6$-fluoroalkoxy, cyano, C(O)$NR_4R_5$, nitro, $NR_4R_5$, $C_1$-$C_6$-thioalkyl, thiol, —S(O)—$C_1$-$C_6$-alkyl, —S(O)$_2$—$C_1$-$C_6$-alkyl, $SO_2NR_4R_5$, $NR_6C(O)R_7$, $NR_6SO_2R_8$, C(O)$NR_4R_5$, OC(O)$NR_4R_5$, —Si—($C_1$-$C_6$-alkyl)$_3$, —$SF_5$, aryl-$C_1$-$C_5$-alkylene or aryl, heteroaryl-$C_1$-$C_5$-alkylene or heteroaryl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy and $C_3$-$C_7$-cycloalkyl-$C_1$-$C_6$-alkylene-O— being optionally substituted with a hydroxyl group, $C_1$-$C_6$-alkoxy or $NR_4R_5$, the aryl and heteroaryl groups being optionally substituted with one or more substituents $R_9$, which may be identical to or different from each other;

$R_1$ is chosen from a hydrogen atom, a halogen atom, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl-$C_1$-$C_3$-alkylenoxy-$C_1$-$C_6$-alkyl, arylthio-$C_1$-$C_6$-alkyl, heteroarylthio-$C_1$-$C_6$-alkyl, aryl-$C_1$-$C_3$-alkylene-thio-$C_1$-$C_6$-alkyl, heteroaryl-$C_1$-$C_3$-alkylene-thio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)$NR_4R_5$, nitro, $NR_4R_5$, $C_1$-$C_6$-thioalkyl, $C_3$-$C_7$-cycloalkylthio, $C_3$-$C_7$-cycloalkyl-$C_1$-$C_3$-alkylene-thio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $SO_2NR_4R_5$, —Si—($C_1$-$C_6$-alkyl)$_3$, —$SF_5$, $NR_6C(O)R_7$, $NR_6SO_2R_8$, C(O)$NR_4R_5$, OC(O)$NR_4R_5$, aryl, heteroaryl, aryl-$C_1$-$C_5$-alkylene, heteroaryl-$C_1$-$C_5$-alkylene, aryloxy, arylthio, heteroaryloxy or heteroarylthio; the heteroaryl or aryl groups being optionally substituted with one or more substituents $R_9$, which may be identical to or different from each other;

$R_2$ represents a hydrogen atom, a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylene-O—, hydroxyl, thiol or $C_1$-$C_6$-fluoroalkoxy;

$R_3$ represents, when it is borne by a carbon atom, a hydrogen atom, a hydroxyl group, thiol, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene, C(O)$NR_4R_5$, C(O)O—$C_1$-$C_6$-alkyl, $CO_2H$, or an oxo or thio group; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene and $C_3$-$C_7$-cycloalkyl-$C_1$-$C_3$-alkylenoxy-$C_1$-$C_3$-alkylene possibly being substituted with a hydroxyl group, $C_1$-$C_6$-alkoxy or $NR_4R_5$; or $R_3$ represents, when it is borne by a nitrogen atom, a hydrogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, aryl-S(O), $C_1$-$C_6$-alkyl-S(O)—, $C_1$-$C_6$-fluoroalkyl-S(O)—, aryl-S(O)$_2$—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $C_1$-$C_6$-alkyl-O—C(O)—, aryl-$C_1$-$C_3$-alkyl-O—C(O)—, $C_3$-$C_7$-cycloalkyl-O—C(O)—, $C_3$-$C_7$-cycloalkyl-$C_1$-$C_3$-alkylene-O—C(O)—, $C_1$-$C_6$-fluoroalkyl-O—C(O)—, aryl-O—C(O)—, heteroaryl-O—C(O)—, heteroaryl or aryl; the heteroaryl and aryl groups being optionally substituted with one or more substituents $R_9$; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, possibly being substituted with a hydroxyl group, $C_1$-$C_6$-alkoxy or $NR_4R_5$;

$R_4$ and $R_5$ represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl, or $R_4$ and $R_5$ together form, with the nitrogen atom that bears them, an azetidine, pyrrolidine, piperidine, azepine, morpholine, thiomorpholine, piperazine or homopiperazine; the group $NR_4R_5$ being optionally substituted with a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$, $C_3$-$C_7$-cycloalkyl-S(O)$_2$—, $C_3$-$C_7$-cycloalkyl-$C_1$-$C_3$-alkylene-S(O)$_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxyl, $C_1$-$C_6$-alkyloxy, $C_3$-$C_7$-cycloalkyloxy, $C_3$-$C_7$-cycloalkyl-$C_1$-$C_3$-alkylenoxy, $C_1$-$C_6$-fluoroalkyl, aryloxy-$C_1$-$C_6$-alkylene, aryloxy, heteroaryloxy-$C_1$-$C_6$-alkylene or heteroaryloxy;

$R_6$ and $R_7$ represent, independently of each other, a hydrogen atom, a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or $R_6$ and $R_7$ together form a 4- to 7-membered lactam comprising the nitrogen atom and the C(O) group that bear them;

$R_8$ represents a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom and a group $C_1$-$C_6$-alkyl, $C_3$-$C_7$-cycloalkyl, $C_3$-$C_7$cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$cycloalkyl-$C_1$-$C_3$-alkylenoxy, $C_1$-$C_6$-fluoroalkoxy, nitro or cyano;

or $R_6$ and $R_8$ together form a 4- to 7-membered sultam comprising the nitrogen atom and the S(O)$_2$ group that bear them;

$R_9$ represents a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy or $C_1$-$C_6$-fluoroalkoxy; these groups being optionally substituted with a group OH, $C_1$-$C_6$-alkoxy or $NR_4R_5$, or alternatively $R_9$ represents a nitro, cyano or $NR_4R_5$ group.

In the compounds of general formula (I):
the sulfur atom(s) may be in oxidized form (S(O) or S(O)$_2$);
the nitrogen atom(s) may optionally be in oxidized form (N-oxide).

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These solvents may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, the following definitions apply:
a halogen atom: a fluorine, a chlorine, a bromine or an iodine;
$C_t$—$C_z$: a carbon-based chain possibly containing from t to z carbon atoms in which t and z may take values from 1 to 7; for example, $C_1$-$C_3$ is a carbon-based chain possibly containing from 1 to 3 carbon atoms;
an alkyl: a linear or branched saturated aliphatic group. Examples that may be mentioned include methyl, ethyl, propyl, isopropyl, butyl, isobutyl, tert-butyl, pentyl, etc.;
an alkylene: a linear or branched saturated divalent alkyl group, for example a group $C_{1-3}$-alkylene represents a linear or branched divalent carbon-based chain of 1 to 3 carbon atoms, more particularly a methylene, ethylene, 1-methylethylene or propylene;
a cycloalkyl: a saturated or partially unsaturated cyclic alkyl group. Examples that may be mentioned include the groups cyclopropyl, cyclobutyl, cyclopentyl, cyclohexyl, etc.;
a cycloalkyloxy: a radical —O-cycloalkyl in which the cycloalkyl group is as defined previously;
a fluoroalkyl: an alkyl group, one or more hydrogen atoms of which have been replaced with a fluorine atom;
an alkoxy: a radical —O-alkyl in which the alkyl group is as defined previously;
a fluoroalkoxy: an alkoxy group, one or more hydrogen atoms of which have been replaced with a fluorine atom;
a thioalkyl or alkylthio: a radical —S-alkyl in which the alkyl group is as defined previously;
an aryl: a monocyclic or bicyclic aromatic group containing between 6 and 10 carbon atoms. Examples of aryl groups that may be mentioned include phenyl and naphthyl groups;
a heteroaryl: a monocyclic or bicyclic aromatic group 5- to 12-membered containing from 1 to 5 heteroatoms chosen from O, S and N.

Examples of monocyclic heteroaryls that may be mentioned include imidazolyl, pyrazolyl, thiazolyl, oxazolyl, isothiazolyl, isoxazolyl, furyl, thiophenyl, oxadiazolyl, thiadiazolyl, triazolyl, tetrazolyl, pyridyl, pyrazinyl, pyrimidinyl, pyridazinyl and triazinyl.

Examples of bicyclic heteroaryls that may be mentioned include indolyl, isoindolyl, benzofuryl, benzothiophenyl, benzoxazolyl, benzimidazolyl, indazolyl, benzothiazolyl, isobenzofuryl, isobenzothiazolyl, pyrrolo[2,3-c]pyridyl, pyrrolo[2,3-b]pyridyl, pyrrolo[3,2-b]pyridyl, pyrrolo[3,2-c]pyridyl, pyrrolo[1,2-a]pyridyl, quinolyl, isoquinolyl, cinnolinyl, quinazolinyl, quinoxalinyl, pyrrolo[1,2-a]imidazolyl, imidazo[1,2-a]pyridyl, imidazo[1,2-a]pyridazinyl, imidazo[1,2-c]pyrimidinyl, imidazo[1,2-a]pyrimidinyl, imidazo[1,2-a]pyrazinyl, imidazo[4,5-b]pyrazinyl, imidazo[4,5-b]pyridyl, imidazo[4,5-c]pyridyl, pyrazolo[2,3-a]pyridyl, pyrazolo[2,3-a]pyrimidinyl and pyrazolo[2,3-a]pyrazinyl.

"oxo" means "=O";
"thio" means "=S".

Among the compounds of general formula (I) that are subjects of the invention, a first subgroup of compounds is constituted by the compounds for which $X_1$, $X_2$, $X_3$ and $X_4$ represent, independently of each other, a group C—$R_1$; $R_1$ being as defined in the general formula (I).

Among the compounds of general formula (I) that are subjects of the invention, a second subgroup of compounds is constituted by the compounds for which one from among $X_1$, $X_2$, $X_3$ and $X_4$ represents a nitrogen atom, the others among $X_1$, $X_2$, $X_3$ and $X_4$ represent, independently of each other, a group C—$R_1$; $R_1$ being as defined in the general formula (I).

Among the compounds of general formula (I) that are subjects of the invention, a third subgroup of compounds is constituted by the compounds for which, among $X_1$, $X_2$, $X_3$ and $X_4$, one from among $X_3$ and $X_4$ represents a nitrogen atom, and the others represent, independently of each other, a group C—$R_1$; $R_1$ being as defined in the general formula (I).

Among the compounds of general formula (I) that are subjects of the invention, a fourth subgroup of compounds is constituted by the compounds for which $R_1$ is chosen from a hydrogen atom, a halogen atom and a group $C_1$-$C_6$-fluoroalkyl or —Si($C_1$-$C_6$-alkyl)$_3$.

Among the compounds of general formula (I) that are subjects of the invention, a fifth subgroup of compounds is constituted by the compounds for which $R_1$ is chosen from a hydrogen atom, a fluorine atom and a group $CF_3$ or $Si(CH_3)_3$.

Among the compounds of general formula (I) that are subjects of the invention, a sixth subgroup of compounds is constituted by the compounds for which n is equal to 1.

Among the compounds of general formula (I) that are subjects of the invention, a seventh subgroup of compounds is constituted by the compounds for which Y represents an aryl or a heteroaryl optionally substituted with one or more groups chosen from a halogen atom, a group $C_1$-$C_6$-alkyl and $C_1$-$C_6$-fluoroalkyl.

Among the compounds of general formula (I) that are subjects of the invention, an eighth subgroup of compounds is constituted by the compounds for which Y represents a phenyl, optionally substituted with one or more groups chosen from a halogen atom and a group $C_1$-$C_6$-alkyl or $C_1$-$C_6$-fluoroalkyl; or alternatively Y represents a pyridyl or a thiazolyl.

Among the compounds of general formula (I) that are subjects of the invention, a ninth subgroup of compounds is constituted by the compounds for which Y represents a phenyl, optionally substituted with a fluorine atom, a methyl group or $CF_3$; or alternatively Y represents a pyridyl or a thiazolyl.

Among the compounds of general formula (I) that are subjects of the invention, a tenth subgroup of compounds is constituted by the compounds for which Y represents a phenyl, optionally substituted with a fluorine atom, a methyl group or $CF_3$.

Among the compounds of general formula (I) that are subjects of the invention, an eleventh subgroup of compounds is constituted by the compounds for which W represents an oxygen atom.

Among the compounds of general formula (I) that are subjects of the invention, a twelfth subgroup of compounds is constituted by the compounds for which $Z_1$, $Z_2$, $Z_3$ and $Z_4$ represent, independently of each other, a nitrogen atom, a carbon atom or a group C—$R_2$, one from among $Z_1$, $Z_2$, $Z_3$ and $Z_4$ corresponding to a nitrogen atom and possibly being in oxidized form;

one from among $Z_1$, $Z_2$, $Z_3$ and $Z_4$, corresponding to a carbon atom, being bonded to the nitrogen atom of the amide or of the thioamide of formula (I);

and the two others from among $Z_1$, $Z_2$, $Z_3$ and $Z_4$ corresponding to a group C—$R_2$;

$R_2$ being as defined in the general formula (I).

Among the compounds of general formula (I) that are subjects of the invention, a thirteenth subgroup of compounds is constituted by the compounds for which $Z_1$, $Z_2$, $Z_3$ and $Z_4$ represent, independently of each other, a nitrogen atom, a carbon atom or a group C—$R_2$, one from among $Z_1$, $Z_2$, $Z_3$ and $Z_4$ corresponding to a nitrogen atom and possibly being in oxidized form;

one from among $Z_1$, $Z_2$, $Z_3$ and $Z_4$, corresponding to a carbon atom, being bonded to the nitrogen atom of the amide or of the thioamide of formula (I);

and the two others from among $Z_1$, $Z_2$, $Z_3$ and $Z_4$ corresponding to a CH group.

Among the compounds of general formula (I) that are subjects of the invention, a fourteenth subgroup of compounds is constituted by the compounds for which Ra and Rb form, together with the carbon atoms that bear them, a 5-membered ring, this ring comprising a nitrogen atom and carbon atoms, this ring being partially saturated or unsaturated and being optionally substituted with one or more substituents $R_3$;

$R_3$ represents, when it is borne by a carbon atom, a hydrogen atom or an oxo group;

$R_3$ represents, when it is borne by a nitrogen atom, a hydrogen atom or a group $C_1$-$C_6$-alkyl or $C_1$-$C_6$-alkyl-C(O)—.

Among the compounds of general formula (I) that are subjects of the invention, a fifteenth subgroup of compounds is constituted by the compounds for which Ra and Rb form, together with the carbon atoms that bear them, a 5-membered ring, this ring comprising a nitrogen atom and carbon atoms, this ring being partially saturated or unsaturated and being optionally substituted with one or more substituents $R_3$;

$R_3$ represents, when it is borne by a carbon atom, a hydrogen atom or an oxo group;

$R_3$ represents, when it is borne by a nitrogen atom, a hydrogen atom, a methyl group or $CH_3$—C(O)—.

Among the compounds of general formula (I) that are subjects of the invention, a sixteenth subgroup of compounds is constituted by the compounds for which the group

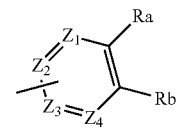

is chosen from the groups

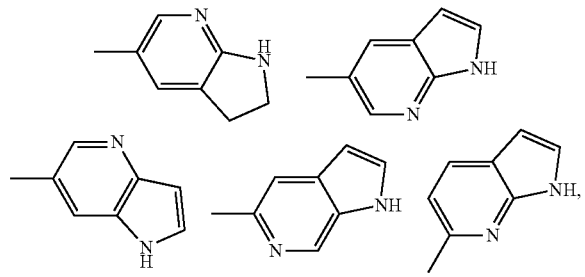

these groups being optionally substituted with $R_2$ and $R_3$ as defined in the general formula (I) hereinabove.

Among the compounds of general formula (I) that are subjects of the invention, a seventeenth subgroup of compounds is constituted by the compounds for which the group

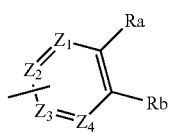

is chosen from the groups

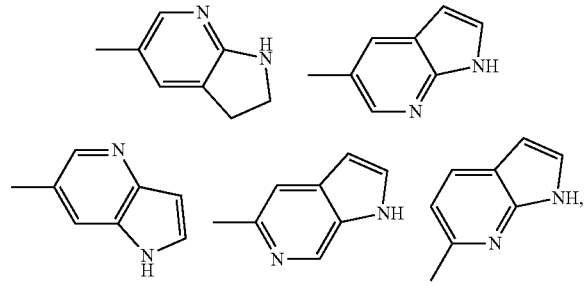

one from among $Z_1$, $Z_2$, $Z_3$ and $Z_4$ corresponding to a nitrogen atom and possibly being in oxidized form;

these groups being optionally substituted with $R_2$ and $R_3$ as defined in the general formula (I);

$R_2$ represents a hydrogen atom;

$R_3$ represents, when it is borne by a carbon atom, a hydrogen atom or an oxo group;

$R_3$ represents, when it is borne by a nitrogen atom, a hydrogen atom or a group $C_1$-$C_6$-alkyl or $C_1$-$C_6$-alkyl-C(O)—.

Among the compounds of general formula (I) that are subjects of the invention, an eighteenth subgroup of compounds is constituted by the compounds for which the group

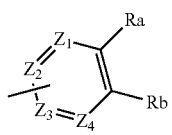

is chosen from the following groups:

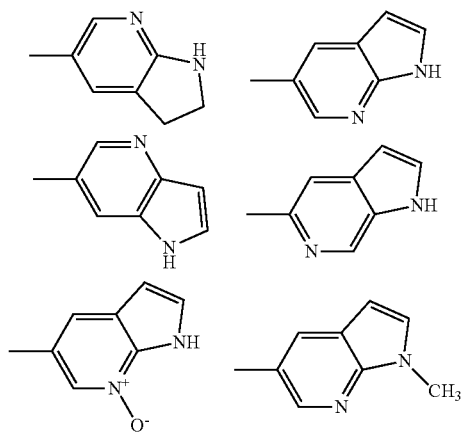

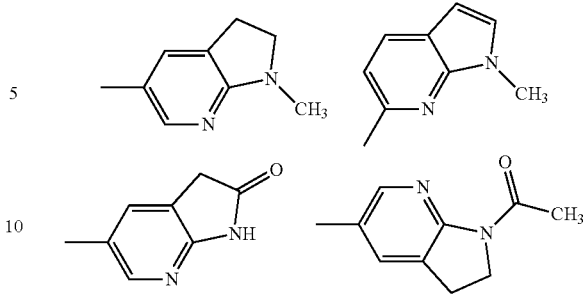

Among the compounds of general formula (I) that are subjects of the invention, a nineteenth subgroup of compounds is constituted by the compounds for which the group

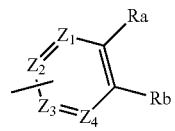

is chosen from the groups

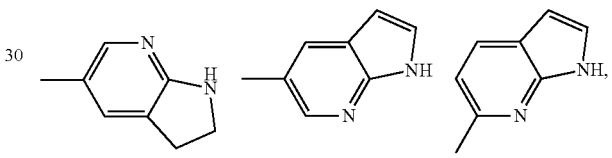

these groups being optionally substituted with $R_2$ and $R_3$ as defined in the general formula (I) hereinabove.

Among the compounds of general formula (I) that are subjects of the invention, a twentieth subgroup of compounds is constituted by the compounds for which the group

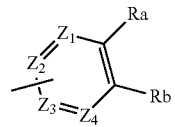

is chosen from the groups

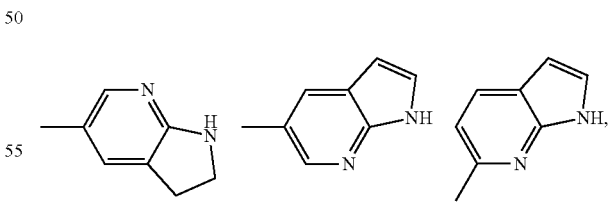

one from among $Z_1$, $Z_2$, $Z_3$ and $Z_4$ corresponding to a nitrogen atom and possibly being in oxidized form;

these groups being optionally substituted with $R_2$ and $R_3$ as defined in the general formula (I);

$R_2$ represents a hydrogen atom;

$R_3$ represents, when it is borne by a carbon atom, a hydrogen atom or an oxo group;

$R_3$ represents, when it is borne by a nitrogen atom, a hydrogen atom or a group $C_1$-$C_6$-alkyl or $C_1$-$C_6$-alkyl-C(O)—.

Among the compounds of general formula (I) that are subjects of the invention, a twenty-first subgroup of compounds is constituted by the compounds for which the group

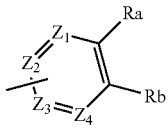

is chosen from the following groups:

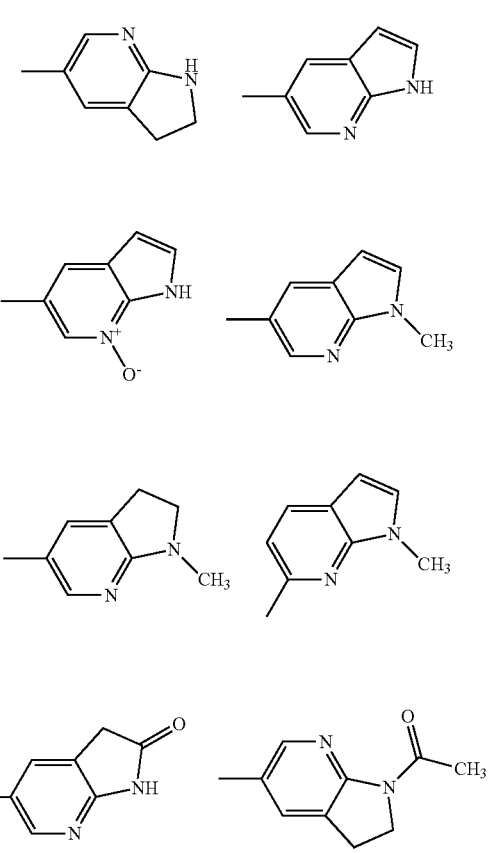

Among the compounds of general formula (I) that are subjects of the invention, a twenty-second subgroup of compounds is constituted by the compounds for which the definitions of $X_1$, $X_2$, $X_3$ and $X_4$, n, Y, W, $Z_1$, $Z_2$, $Z_3$, $Z_4$; Ra and Rb given hereinabove are combined.

Among the compounds of general formula (I) that are subjects of the invention, a twenty-third subgroup of compounds is constituted by the compounds for which either $X_1$, $X_2$, $X_3$ and $X_4$ represent, independently of each other, a group C—$R_1$; or, among $X_1$, $X_2$, $X_3$ and $X_4$, one from among $X_3$ and $X_4$ represents a nitrogen atom and the others represent, independently of each other, a group C—$R_1$;

$R_1$ is chosen from a hydrogen atom, a halogen atom and a group $C_1$-$C_6$-fluoroalkyl or —Si($C_1$-$C_6$-alkyl)$_3$;

n is equal to 1;

Y represents a phenyl, optionally substituted with one or more groups chosen from a halogen atom and a group $C_1$-$C_6$-alkyl or $C_1$-$C_6$-fluoroalkyl; or alternatively Y represents a pyridyl or a thiazolyl;

W represents an oxygen atom;
the group

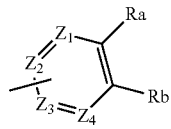

is chosen from the groups

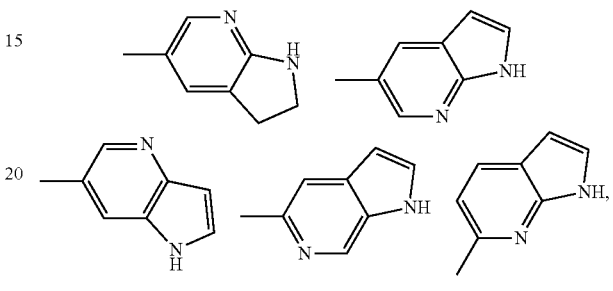

one from among $Z_1$, $Z_2$, $Z_3$ and $Z_4$ corresponding to a nitrogen atom and possibly being in oxidized form;

these groups being optionally substituted with $R_2$ and $R_3$ as defined in the general formula (I);

$R_2$ represents a hydrogen atom;

$R_3$ represents, when it is borne by a carbon atom, a hydrogen atom or an oxo group;

$R_3$ represents, when it is borne by a nitrogen atom, a hydrogen atom or a group $C_1$-$C_6$-alkyl or $C_1$-$C_6$-alkyl-C(O)—.

Among the compounds of general formula (I) that are subjects of the invention, a twenty-fourth subgroup of compounds is defined such that
the compounds for which $X_1$, $X_2$, $X_3$ and $X_4$ represent, independently of each other, a group C—$R_1$;

$R_1$ is chosen from a hydrogen atom, a halogen atom, a group $C_1$-$C_6$-alkyl, $C_1$-$C_6$-fluoroalkyl, $C_1$-$C_6$-alkoxy, $C_1$-$C_6$-fluoroalkoxy, $NR_4R_5$, $C_1$-$C_6$-thioalkyl, phenyl or isoxazolyl; the phenyl group being optionally substituted with one or more substituents $R_9$, which may be identical to or different from each other;

$R_4$ and $R_5$ represent, independently of each other, a hydrogen atom or a group $C_1$-$C_6$-alkyl, W represents an oxygen atom;

n is equal to 0;

Y represents a phenyl optionally substituted with one or more substituents $R_9$, which may be identical to or different from each other; or Y represents an isoxazole;

$R_9$ represents a halogen atom or a group $C_1$-$C_6$-alkyl, $C_1$-$C_6$-alkoxy or cyano;
the group

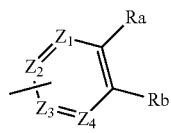

represents the group D:

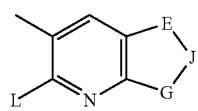

in which

L represents a hydrogen atom, a halogen atom or a group $C_1$-$C_4$-alkoxy;

the 5-membered ring is partially saturated or unsaturated; J represents N or C=O;

when J represents N, then E and G represent, independently of each other, a group C=O or $CH_2$; when J represents C=O, one from among E and G represents a group C=O or $CH_2$, and the other from among E and G represents a group N—R'; R' represents a hydrogen atom or a group $C_1$-$C_4$-alkyl or aryl-C(O)—, the aryl group being optionally substituted with one or more groups $C_1$-$C_6$-alkyl;

are excluded.

Among the compounds of general formula (I) that are subjects of the invention, a twenty-fifth subgroup of compounds is constituted by the compounds for which $X_1$, $X_2$, $X_3$ and $X_4$ represent, independently of each other, a group C—$R_1$; and $R_1$ is chosen from a hydrogen atom and a halogen atom, more particularly a fluorine atom.

Among the compounds of general formula (I) that are subjects of the invention, a twenty-sixth subgroup of compounds is constituted by the compounds for which n is equal to 1 and Y represents an aryl, more particularly a phenyl, optionally substituted with one or more halogen atoms, more particularly fluorine atoms.

Among the compounds of general formula (I) that are subjects of the invention, a twenty-seventh subgroup of compounds is constituted by the compounds for which W represents an oxygen atom.

Among the compounds of general formula (I) that are subjects of the invention, a twenty-eighth subgroup of compounds is constituted by the compounds for which the group

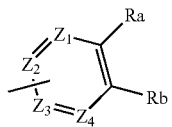

is chosen from the groups

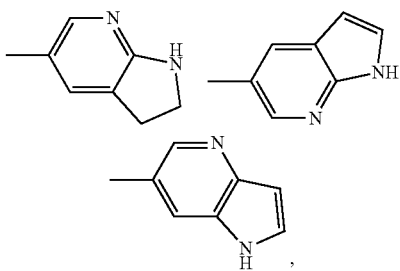

these groups being optionally substituted with $R_2$ and $R_3$ as defined in the general formula (I) hereinabove.

Among the compounds of general formula (I) that are subjects of the invention, a twenty-ninth subgroup of compounds is constituted by the compounds for which $X_1$, $X_2$, $X_3$ and $X_4$ represent, independently of each other a group C—$R_1$; and $R_1$ is chosen from a hydrogen atom and a halogen atom, more particularly a fluorine atom;

n is equal to 1;

Y represents an aryl, more particularly a phenyl, optionally substituted with one or more halogen atoms, more particularly fluorine atoms;

W represents an oxygen atom;

the group

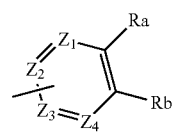

is chosen from the groups

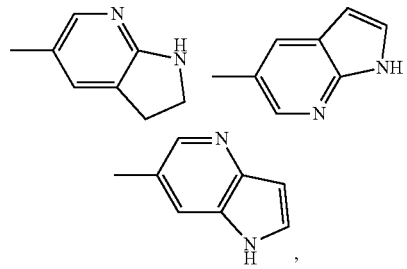

these groups being optionally substituted with $R_2$ and $R_3$ as defined in the general formula (I) hereinabove.

Among the compounds of general formula (I) that are subjects of the invention, mention may be made especially of the following compounds:

1 N-(1-acetyl-2,3-dihydro-1H-pyrrolo[2,3-b]pyrid-5-yl)-5-fluoro-1-(3-fluorobenzyl)-1H-indole-2-carboxamide 2 N-(1H-pyrrolo[2,3-b]pyrid-5-yl)-5-fluoro-1-(3-fluorobenzyl)-1H-indole-2-carboxamide 3 N-(2,3-dihydro-1H-pyrrolo[2,3-b]pyrid-5-yl)-5-fluoro-1-(3-fluorobenzyl)-1H-indole-2-carboxamide 4 N-(1H-pyrrolo[3,2-b]pyrid-6-yl)-5-fluoro-1-(3-fluorobenzyl)-1H-indole-2-carboxamide 5 N-(1H-Pyrrolo[2,3-b]pyrid-5-yl)-6-fluoro-1-[(3-methylphenyl)methyl]-1H-indole-2-carboxamide 6 N-(1H-Pyrrolo[2,3-b]pyrid-5-yl)-6-trimethylsilyl-1-[[(3-trifluoromethyl)phenyl]-methyl]-1H-indole-2-carboxamide 7 N-(1H-Pyrrolo[2,3-b]pyrid-5-yl)-5-trimethylsilyl-1-[[(3-trifluoromethyl)phenyl]-methyl]-1H-indole-2-carboxamide 8 N-(1H-Pyrrolo[2,3-c]pyrid-5-yl)-5-fluoro-1-[(3-fluorophenyl]methyl]-1H-indole-2-carboxamide 9 N-(1H-Pyrrolo[2,3-b]pyrid-5-yl)-5-trifluoromethyl-1-[(3-fluorophenyl)methyl]-1H-pyrrolo[2,3-b]pyridine-2-carboxamide 10 N-(7-Oxy-1H-pyrrolo[2,3-b]pyrid-5-yl)-5-fluoro-1-[(3-fluorophenyl)methyl]-1H-indole-2-carboxamide 11 N-(1-Methyl-1H-pyrrolo[2,3-b]pyrid-5-yl)-5-trifluoromethyl-1-[(3-fluorophenyl)-methyl]-1H-indole-2-carboxamide 12 N-(1-Methyl-1H-pyrrolo[2,3-b]pyrid-5-yl)-5-fluoro-1-[(3-fluorophenyl)methyl]-1H-indole-2-carboxamide
13 N-(1-Methyl-1H-pyrrolo[2,3-b]pyrid-5-yl)-5-trifluoromethyl-1-[(3-fluorophenyl)-methyl]-1H-pyrrolo[2,3-b]pyridine-2-carboxamide
14 N-(1-Methyl-2,3-dihydro-1H-pyrrolo[2,3-b]pyrid-5-yl)-5-fluoro-1-[(3-fluorophenyl)-methyl]-1H-indole-2-carboxamide
15 N-(1-Methyl-1H-pyrrolo[2,3-b]pyrid-5-yl)-1-[[(3-trifluoromethyl)phenyl]methyl]-1H-indole-2-carboxamide
16 N-(1-Methyl-1H-pyrrolo[2,3-b]pyrid-6-yl)-5-fluoro-1-[(3-fluorophenyl)methyl]-1H-indole-2-carboxamide
17 N-(1-Methyl-1H-pyrrolo[2,3-b]pyrid-5-yl)-5-fluoro-1-[[(3-trifluoromethyl)phenyl]-methyl]-1H-indole-2-carboxamide
18 N-(1-Methyl-1H-pyrrolo[2,3-b]pyrid-5-yl)-5-fluoro-1-[(3-methylphenyl)methyl]-1H-indole-2-carboxamide
19 N-(1H-pyrrolo[2,3-b]pyrid-5-yl)-5-trifluoromethyl-1-[(3-methylphenyl)methyl]-1H-indole-2-carboxamide
20 N-(1H-pyrrolo[2,3-b]pyrid-5-yl)-6-trifluoromethyl-1-[(3-methylphenyl)methyl]-1H-indole-2-carboxamide
21 N-(1H-pyrrolo[2,3-b]pyrid-5-yl)-5-trimethylsilyl-1-[(3-methylphenyl)methyl]-1H-indole-2-carboxamide
22 N-(1H-pyrrolo[2,3-b]pyrid-5-yl)-5-trifluoromethyl-1-[(3-methylphenyl)methyl]-1H-pyrrolo[2,3-b]pyridine-2-carboxamide
23 N-(1H-pyrrolo[2,3-b]pyrid-5-yl)-6-trimethylsilyl-1-[(3-methylphenyl)methyl]-1H-indole-2-carboxamide
24 N-(1H-Pyrrolo[2,3-b]pyrid-5-yl)-5-trifluoromethyl-1-[[(3-trifluoromethyl)phenyl]-methyl]-1H-indole-2-carboxamide
25 N-(1H-Pyrrolo[2,3-b]pyrid-5-yl)-6-trifluoromethyl-1-[[(3-trifluoromethyl)phenyl]-methyl]-1H-indole-2-carboxamide
26 N-(1H-pyrrolo[2,3-b]pyrid-5-yl)-5-trifluoromethyl-1-[[(3-trifluoromethyl)phenyl]-methyl]-1H-pyrrolo[2,3-b]pyridine-2-carboxamide
27 N-(1H-Pyrrolo[2,3-b]pyrid-5-yl)-6-fluoro-1-[[(3-trifluoromethyl)phenyl]methyl]-1H-indole-2-carboxamide
28 N-(1-Methyl-1H-pyrrolo[2,3-b]pyrid-5-yl)-5-fluoro-1-[(pyrid-4-yl)methyl)]-1H-indole-2-carboxamide
29 N-(1-Methyl-1H-pyrrolo[2,3-b]pyrid-5-yl)-5-fluoro-1-[(pyrid-3-yl)methyl)]-1H-indole-2-carboxamide
30 N-(1H-Pyrrolo[2,3-b]pyrid-5-yl)-5-trifluoromethyl-1-[(thiazol-2-yl)methyl]-1H-pyrrolo[2,3-b]pyridine-2-carboxamide
31 N-(1H-Pyrrolo[2,3-b]pyrid-5-yl)-6-trimethylsilyl-1-[(thiazol-2-yl)methyl]-1H-indole-2-carboxamide
32 N-(1H-Pyrrolo[2,3-b]pyrid-5-yl)-5-trifluoromethyl-1-[(thiazol-2-yl)methyl]-1H-indole-2-carboxamide
33 N-(1H-Pyrrolo[2,3-b]pyrid-5-yl)-6-trifluoromethyl-1-[(thiazol-2-yl)methyl]-1H-indole-2-carboxamide
34 N-(1H-Pyrrolo[2,3-b]pyrid-5-yl)-5-trimethylsilyl-1-[(thiazol-2-yl)methyl]-1H-indole-2-carboxamide
35 N-(1H-Pyrrolo[2,3-b]pyrid-5-yl)-6-fluoro-1-[(thiazol-2-yl)methyl]-1H-indole-2-carboxamide
36 N-(1H-Pyrrolo[2,3-b]pyrid-5-yl)-5-trifluoromethyl-1-[(pyrid-4-yl)methyl)]-1H-indole-2-carboxamide
37 N-(1H-Pyrrolo[2,3-b]pyrid-5-yl)-6-trifluoromethyl-1-[(pyrid-4-yl)methyl)]-1H-indole-2-carboxamide
38 N-(1H-Pyrrolo[2,3-b]pyrid-5-yl)-6-trimethylsilyl-1-[(pyrid-4-yl)methyl)]-1H-indole-2-carboxamide
39 N-(1H-Pyrrolo[2,3-b]pyrid-5-yl)-5-trimethylsilyl-1-[(pyrid-4-yl)methyl)]-1H-indole-2-carboxamide
40 N-(1H-Pyrrolo[2,3-b]pyrid-5-yl)-6-fluoro-1-[(pyrid-4-yl)methyl)]-1H-indole-2-carboxamide
41 N-(1H-Pyrrolo[2,3-b]pyrid-5-yl)-5-trifluoromethyl-1-[(pyrid-4-yl)methyl)]-1H-pyrrolo[2,3-b]pyridine-2-carboxamide
42 N-(2-Oxo-2,3-dihydro-1H-pyrrolo[2,3-b]pyrid-5-yl)-5-fluoro-1-[(3-fluorophenyl)methyl]-1H-indole-2-carboxamide
43 N-(1H-Pyrrolo[2,3-b]pyrid-5-yl)-5-trifluoromethyl-1-[(3-fluorophenyl)methyl]-1H-indole-2-carboxamide
44 N-(1-Methyl-1H-pyrrolo[2,3-b]pyrid-5-yl)-1-[(3-fluorophenyl)methyl]-1H-pyrrolo[2,3-c]pyridine-2-carboxamide
45 N-(1H-pyrrolo[2,3-b]pyrid-5-yl)-1-[(3-fluorophenyl)methyl]-1H-pyrrolo[2,3-c]pyridine-2-carboxamide
46 N-(1H-Pyrrolo[2,3-b]pyrid-5-yl)-5-fluoro-1-[(pyrid-4-yl)methyl)]-1H-indole-2-carboxamide
47 N-(1-Methyl-1H-Pyrrolo[2,3-b]pyrid-5-yl)-5-trifluoromethyl-1-[(pyrid-4-yl)methyl)]-1H-indole-2-carboxamide.

In the text hereinbelow, the term "leaving group" means a group that can be readily cleaved from a molecule by breaking a heterolytic bond, with loss of an electron pair. This group may thus be readily replaced by another group during a substitution reaction, for example. Such leaving groups are, for example, halogens or an activated hydroxyl group such as a methanesulfonate, benzenesulfonate, p-toluenesulfate, triflate, acetate, etc. Examples of leaving groups and references for preparing them are given in "Advances in Organic Chemistry", J. March, 5th Edition, Wiley Interscience, 2001.

In the text hereinbelow, the term "protecting group" means a group that can be momentarily incorporated into a chemical structure for the purpose of temporarily inactivating a part of the molecule during a reaction, and which may be readily removed in a subsequent synthetic step. Examples of protecting groups and references concerning their properties are given in T. W. Greene, P. G. M. Wutz, 3rd Edition, Wiley Interscience 1999.

In accordance with the invention, the compounds of general formula (I) may be prepared according to the process illustrated by the general scheme 1 below:

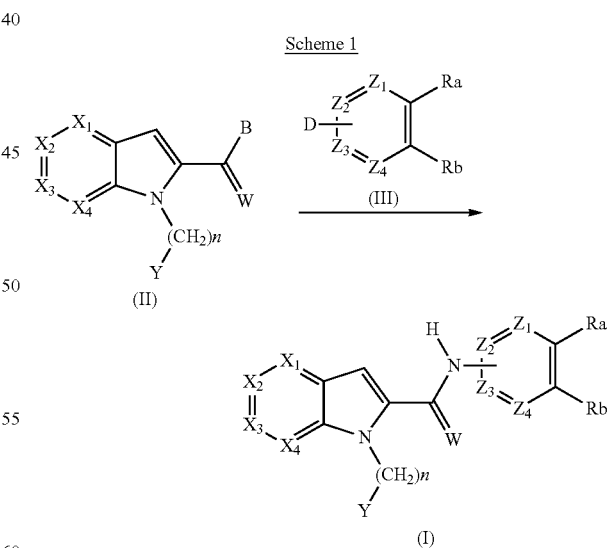

The compounds of general formula (I) may be obtained by reacting a compound of general formula (II), in which $X_1$, $X_2$, $X_3$, $X_4$, n, Y and W are as defined in the general formula (I) hereinabove and B corresponds to a hydroxyl group, with an amine of general formula (III), in which $Z_1$, $Z_2$, $Z_3$, $Z_4$, Ra and Rb are as defined in the general formula (I) hereinabove and D corresponds to an amino group, in the presence of a coupling agent such as a dialkylcarbodiimide, [(benzotriazol-1-yl)oxy][tris(pyrrolidino)]-phosphonium hexafluorophosphate, diethyl cyanophosphonate or any other coupling agent known to those skilled in the art, optionally in the presence of a base such as triethylamine, in a solvent, for instance dimethylformamide.

The compound of general formula (II), for which B represents a group $C_1$-$C_6$-alkoxyl, may be converted into a compound of general formula (II), in which B represents a hydroxyl group, via the action of a base such as sodium hydroxide or potassium hydroxide dissolved in a solvent such as ethanol. The compound of general formula (II) in which B represents a hydroxyl group may then be converted into a compound of general formula (II), in which B represents a chlorine atom, via the action of a chlorinating agent such as thionyl chloride in a solvent such as dichloromethane.

The compounds of general formula (I) may be obtained by reacting a compound of general formula (II), in which $X_1$, $X_2$, $X_3$, $X_4$, n, Y and W are as defined in the general formula (I) hereinabove and B corresponds to a chlorine atom, with an amine of general formula (III), in which $Z_1$, $Z_2$, $Z_3$, $Z_4$, Ra and Rb are as defined in the general formula (I) hereinabove and D correspond to an amino group, via reaction in solution in a solvent such as dichloromethane or toluene.

The compounds of general formula (I) may also be obtained by reacting a compound of general formula (II) in which $X_1$, $X_2$, $X_3$, $X_4$, n, Y and W are as defined in the general formula (I) hereinabove and B corresponds to a group $C_1$-$C_6$-alkoxyl, with an amide, resulting from (III), in which $Z_1$, $Z_2$, $Z_3$, $Z_4$, Ra and Rb are as defined in the general formula (I) hereinabove and D corresponds to an amino group, and an organometallic reagent such as trimethylaluminium. This reaction may be performed in a solvent such as toluene.

Starting with compounds of general formula (II), in which B represents an $NH_2$ group, W represents an oxygen atom and $X_1$, $X_2$, $X_3$, $X_4$, n and Y are as defined in the general formula (I) hereinabove, the compound of general formula (I) may be obtained by reaction with the compound of general formula (III), in which $Z_1$, $Z_2$, $Z_3$, $Z_4$, Ra and Rb are as defined in the general formula (I) hereinabove and D corresponds to a leaving group as defined hereinabove, such as a bromine atom or a triflate group, for example according to a method similar to that described in J. Am. Chem. Soc. 2001, 123 (31), 7727, or according to methods described in the literature or known to those skilled in the art, in the presence of a copper salt in catalytic amount, in the presence of a catalytic amount of a copper ligand, such as a diamine, the whole in the presence of a base such as potassium carbonate, in a solvent such as dioxane.

In Scheme 1, the compounds of general formula (I) and the other reagents, when their mode of preparation is not described, are commercially available, are described in the literature or are prepared by analogy with processes described in the literature (D. Knittel Synthesis 1985, 2, 186; T. M. Williams J. Med. Chem. 1993, 36 (9), 1291; JP2001-151 771 A2, WO2006/024776, WO2006/072736, WO2007/010144, WO2007/010138 or WO2007/088277, for example).

The compounds of general formula (III), when their mode of preparation is not described, are commercially available, are described in the literature or are prepared by analogy with processes described in the literature (Tetrahedron Lett. 1987, 1589, Synthesis 2005, 15, 2503, Synthesis 2008, 2, 201, WO2006/040520).

The compounds of general formula (II) or (I), for which one from among $X_1$, $X_2$, $X_3$ and $X_4$ corresponds to a carbon atom substituted with an alkyl group, may be obtained via a coupling reaction, catalysed by a metal such as palladium or iron, performed on the corresponding compounds of general formula (II) or (I), substituted with a halogen atom, such as chlorine, in the presence, for example, of an alkylmagnesium halide or an alkylzinc halide, according to the methods described in the literature (A. Furstner et al., J. Am. Chem. Soc. 2002, 124(46), 13856; G. Queguiner et al., J. Org. Chem. 1998, 63(9), 2892) for example, or known to those skilled in the art.

The compounds of general formula (II) or (I), for which one from among $X_1$, $X_2$, $X_3$ and $X_4$ corresponds to a carbon atom substituted with a cyano, aryl or heteroaryl group, may be obtained via a coupling reaction, catalysed with a metal such as palladium, performed on the corresponding compounds of general formula (II) or (I), substituted, for example, with a bromine atom, in the presence of trimethylsilyl cyanide, an arylboronic acid or a heteroarylboronic acid, or via any other method described in the literature or known to those skilled in the art.

The compounds of general formula (I) or (II), for which one from among $X_1$, $X_2$, $X_3$ and $X_4$ corresponds to a carbon atom substituted with a group $NR_4R_5$, $NR_6COR_7$ or $NR_6SO_2R_8$, may be obtained from the corresponding compounds of general formula (I) or (II), substituted, for example, with a bromine atom, via a coupling reaction with, respectively, an amine, an amide or a sulfonamide in the presence of a base, a phosphine and a palladium-based catalyst, according to methods described in the literature or known to those skilled in the art.

The compounds of general formula (I) or (II) substituted with a group $C(O)NR_4R_5$ may be obtained from the corresponding compounds of general formula (I) or (II) substituted with a cyano group, according to methods described in the literature or known to those skilled in the art.

The compounds of general formula (I) or (II) substituted with a group —S(O)-alkyl or —S(O)$_2$-alkyl may be obtained via oxidation of the corresponding compounds of general formula (II) or (I), substituted with a thioalkyl group, according to methods described in the literature or known to those skilled in the art.

The compounds of general formula (II) or (I) substituted with a group $NR_4R_5$, $NR_6COR_7$ or $NR_6SO_2R_8$ may be obtained from the corresponding compounds of general formula (II) or (I), substituted with a nitro group, for example via reduction, followed by acylation or sulfonylation, according to methods described in the literature or known to those skilled in the art.

The compounds of general formula (II) or (I) substituted with a group $SO_2NR_4R_5$ may be obtained via a method similar to that described in Pharmazie 1990, 45, 346, or according to methods described in the literature or known to those skilled in the art.

The compounds of general formula (I) or (II) in which W represents a sulfur atom may be obtained, for example, by reacting the corresponding compounds of general formula (I) or (II), in which W represents an oxygen atom, with a reagent such as Lawesson's reagent.

The compounds of general formula (I) for which $R_3$ corresponds to a protecting group borne by a nitrogen atom, such as an acetyl, ethoxycarbonyl or tert-butyloxycarbonyl group or a benzyloxycarbonyl group, may be deprotected, according to chemical methods known to those skilled in the art, to give compounds of general formula (I) in which $R_3$ is a hydrogen atom.

The compounds of general formula (I), in which at least one from among $Z_1$, $Z_2$, $Z_3$ and $Z_4$ corresponds to an N-oxide group, may be obtained, for example, by reacting the corresponding compounds of general formula (I) in which at least one from among $Z_1$, $Z_2$, $Z_3$ and $Z_4$ corresponds to a nitrogen atom, with a reagent such as meta-chloroperbenzoic acid.

The compounds of general formula (II) of Scheme 1, in which one from among $X_1$, $X_2$, $X_3$ and $X_4$ represents a group C—$R_1$ in which $R_1$ corresponds to a group —Si—$(C_1$-$C_6$-alkyl$)_3$ and B represents a group $C_1$-$C_6$-alkoxyl, may be obtained, for example, according to the methods illustrated in Scheme 2.

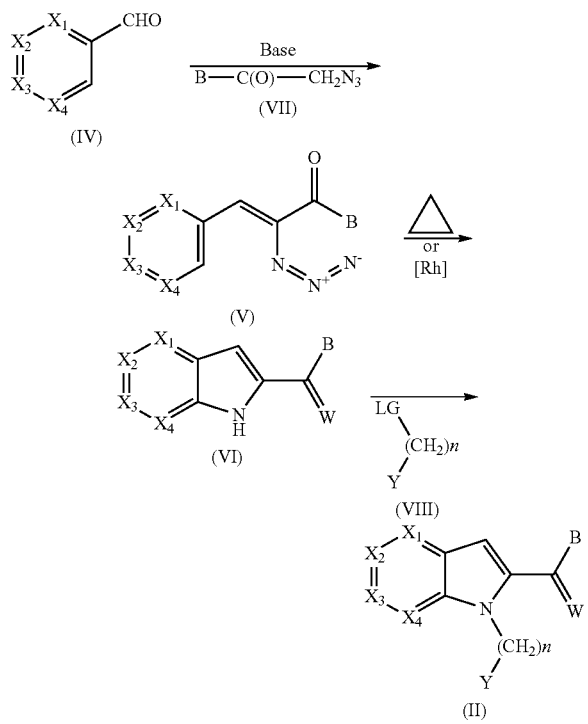

According to this method, the compounds of general formula (II), defined such that n is equal to 1, 2 or 3, are obtained by reaction of the corresponding compounds of general formula (VI) with a reagent of general formula (VIII), in which LG represents a leaving group such as a chlorine, bromine or iodine atom and n is equal to 1, 2 or 3. The reaction for the formation of the compounds of general formula (II) may be performed in the presence of a base such as sodium hydride or potassium carbonate, in a polar solvent such as dimethylformamide, dimethyl sulfoxide or acetone (n=1: Kolasa T., Bioorg. Med. Chem. 1997, 5 (3) 507, n=2: Abramovitch R., Synth. Commun., 1995, 25 (1), 1).

When the compound of general formula (VIII) is defined such that n is equal to 1, 2 or 3 and LG represents a hydroxyl group, the compounds of general formula (II) may be obtained by reacting the compound of general formula (VI) with a compound of general formula (VIII) in the presence of a phosphine, for instance triphenylphosphine, and a reagent, for instance diethyl azodicarboxylate, dissolved in a solvent such as dichloromethane or tetrahydrofuran (O. Mitsonobu, Synthesis, 1981, 1-28).

Similarly, the compounds of general formula (II) may be obtained by reacting the compound of general formula (VI) with a compound of general formula (VIII) in the presence of a phosphine supported on a resin and of a reagent such as, for example, diisopropyl azodicarboxylate, dissolved in a solvent such as dichloromethane or tetrahydrofuran.

When the compound of general formula (VIII) is defined such that n is equal to 0 and LG represents a leaving group such as a chlorine, bromine or iodine atom, the reaction for formation of the compounds of general formula (II) may be performed by application or adaptation of the methods described by S. L. Buchwald et al. (*J. Am. Chem. Soc.*, 2001, 123, 7727 and 2002, 124, 11684), preferably under an inert atmosphere in basic medium, for example in the presence of potassium triphosphate, in the presence of a copper salt such as copper iodide, optionally in the presence of an additive such as N,N'-dimethylcyclohexane-1,2-diamine, the whole in an organic solvent such as toluene.

The compounds of general formula (VI) are prepared from aromatic or heteroaromatic aldehydes substituted with a silyl group of general formula (IV), in which $X_1$, $X_2$, $X_3$ and $X_4$ are as defined in the general formula (I) with one of them corresponding to a silyl group, by reaction with an alkyl azidoacetate of general formula (VII) in which B represents a group $C_1$-$C_6$-alkoxyl, for instance ethyl azidoacetate, in the presence of a base such as sodium ethoxide, in a solvent such as ethanol or methanol, to give the alkyl 2-azidocinnamates of general formula (V). These products are then converted into indole or azaindole esters in a refluxing solvent, for example in xylene or toluene, by adaptation of the protocols described in the literature (Hemetsberger et al., *Monatsh. Chem.*, 1969, 100, 1599 and 1970, 101, 161; P. Roy et al., *Synthesis.*, 2005, 16, 2751-2757; R. Guilard et al., *J. Heterocyclic. Chem.*, 1981, 18, 1365-1377; W. Rees et al., *J. Chem. Soc., Perkin Trans.* 1 1984, 2189-2196; P. Molina et al., *J. Org. Chem.*, 2003, 68(2), 489-499; C. Moody et al., *J. Chem. Soc., Perkin Trans.* 1 1984, 2189-2196; J. Sawyer et al., *J. Med. Chem.*, 2005, 48, 893-896; D. Tanner Synlett 2006, 18, 3140-3144).

Alternatively, the formation of the compounds of general formula (VI) may be obtained by decomposition of the alkyl 2-azidocinnamate of general formula (V), in the presence of a rhodium dimer complex, in a solvent such as toluene, at a temperature of between 25° C. and 60° C., according to an adaptation of protocols described in the literature (Tom G. Drivers et al., *J. Am. Chem. Soc.*, 2007, 129, 7500-7501; J. Sawyer et al., *J. Med. Chem.*, 2005, 48, 893-896).

The aromatic or heteroaromatic aldehydes substituted with a silyl group of general formula (IV), when they are not commercially available, may be obtained from the corresponding aromatic or heteroaromatic aldehydes, which are preferably masked in the form of an acetal, for example, substituted with a halogen atom such as a bromine or an iodine, in the position at which the silyl group is to be introduced:

for example by reaction with a disilane such as hexamethyldisilane, in the presence of a catalytic amount of a metal complex, preferably a palladium complex, for instance tetrakis(triphenylphosphine)palladium, without solvent or in a solvent, preferably a polar solvent, for instance hexamethylphosphoramide, in the presence of a base such as potassium carbonate, at a temperature of between 20° C. and the boiling point of the solvent (adaptation of the protocols described in the literature: J. Babin et al., *J. Organometall. Chem.*, 1993, 446 (1-2), 135-138; E. Shirakawa et al., *Chem. Commun.*, 2000, 1895-1896; L. Goossen et al., *Synlett*, 2000, 1801-1803; H. Matsumoto et al., *J. Organometall. Chem.*, 1975, 85, Cl; FR 2 677 358).

for example by reaction with a disilane such as hexamethyldisilane, in the presence of a strong base, for instance hexamethylphosphorotriamide (HMPT), at a temperature close to 20° C. (adaptation of the protocols described in the literature: A. I. Meyers et al., *J. Org. Chem.*, 1977, 42 (15), 2654-2655; K. Ishimaru et al., *Heterocycles.*, 2001, 55 (8), 1591-1597).

The aromatic or heteroaromatic aldehydes substituted with a silyl group of general formula (IV), when they are not commercially available, may also be obtained from the corresponding dihalo aromatic or heteroaromatic derivatives, such as a dibromo derivative, in the position at which the silyl group is to be introduced, by exchange with an organometallic reagent, for instance n-butyllithium. The metallic aromatic or heteroaromatic derivatives thus formed may then react with organohalosilanes or may be converted into formyl derivatives by adaptation of the methods described in the literature. The reaction is preferably performed at low temperatures of between −110° C. and room temperature, in a solvent such as ether or THF (adaptation of the protocols described in the literature: Bao-Hui Ye et al., *Tetrahedron.*, 2003, 59, 3593-3601; P. Pierrat et al., *Synlett* 2004, 13, 2319-2322; K. T. Warner et al., *Heterocycles* 2002, 58, 383; D. Deffieux et al., *J. Organometall. Chem.*, 1994, 13 (6), 2415-2422; WO2005/080 28; S. G. Davies et al., *J. Chem. Soc., Perkin Trans.* 1 1991, 501; G. Queguiner et al., *J. Org. Chem.*, 1981, 46, 4494-4497; G. Breton et al., *Tetrahedron* 2000, 56 (10), 1349-1360; S. De Montis et al., *Tetrahedron* 2004, 60 (17), 3915-3920; L. Buchwald et al., *J. Am. Chem. Soc.*, 1998, 120, 4960-4976).

According to another of its aspects, a subject of the invention is also the compounds of general formulae (IIa), (IIb), (IIc), (IId), (IIe), (IIf), (IIg) and (IIh), in which Et represents an ethyl group. These compounds are useful as intermediates for the synthesis of the compounds of formula (I).

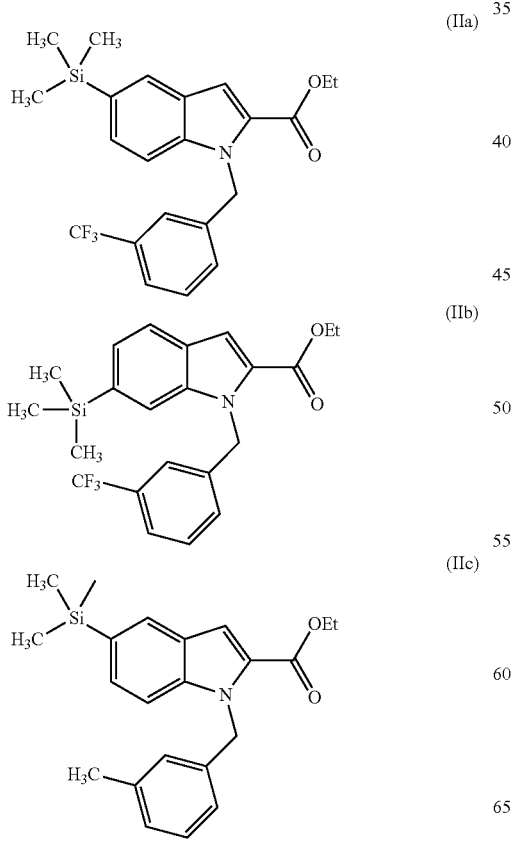

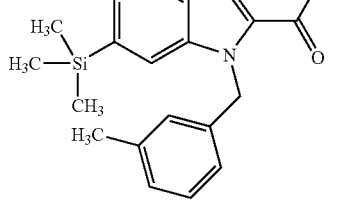

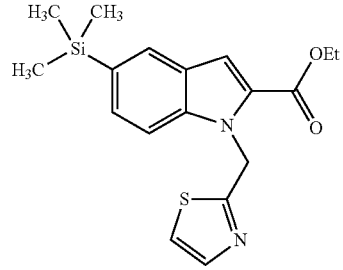

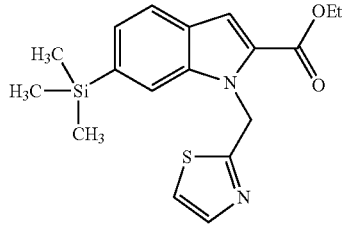

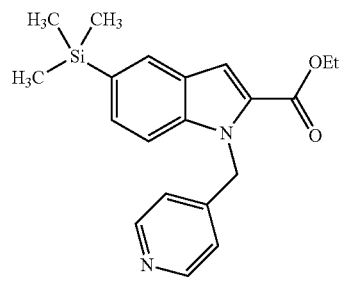

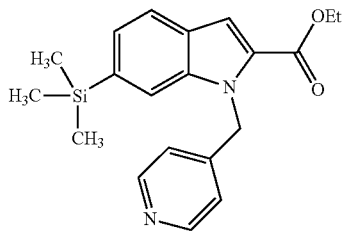

The esters (IIa), (IIb), (IIc), (IId), (IIe), (IIf), (IIg) and (IIh) are prepared according to the processes described in Examples 9, 10, 14, 16, 21, 38, 40 and 41.

The examples that follow describe the preparation of certain compounds in accordance with the invention. These examples are not limiting, and serve merely to illustrate the present invention. The numbers of the illustrated compounds refer to those in Table 1. The elemental microanalyses, the LC-MS analyses (liquid chromatography coupled to mass spectrometry) and the IR or NMR spectrum confirm the structures of the compounds obtained.

EXAMPLE 1

Compound 1

N-[1-Acetyl-2,3-dihydro-1H-pyrrolo[2,3-b]pyrid-5-yl]-5-fluoro-1-[(3-fluorophenyl)-methyl]-1H-indole-2-carboxamide

1.1
5-Fluoro-1-(3-fluorobenzyl)-1H-indole-2-carboxylic acid

An aqueous sodium hydroxide solution, prepared from 1.15 g (28.92 mmol) of sodium hydroxide pellets in 50 mL of water, is added to a solution of 7.6 g (24.10 mmol) of ethyl 5-fluoro-1-(3-fluorobenzyl)-1H-indole-2-carboxylate (WO2006/024776) in 241 mL of ethanol. The mixture is heated for 2 hours and then concentrated under reduced pressure. The resulting solid is taken up in 200 mL of water. The solution is washed with twice 100 mL of ethyl ether, acidified by successive addition of small amounts of concentrated hydrochloric acid and then extracted with 200 mL of ethyl acetate. The organic phase is finally washed twice with 100 mL of water, once with 50 mL of saturated sodium chloride solution, dried over magnesium sulfate and concentrated under reduced pressure. After drying at 50° C. under reduced pressure, 6.4 g of the expected product are obtained in the form of a solid, which is used without further purification in the rest of the synthesis.

1.2 1-Acetyl-5-amino-2,3-dihydro-1H-pyrrolo[2,3-b]pyridine

A suspension of 0.43 g (2.08 mmol) of 1-acetyl-2,3-dihydro-5-nitro-1H-pyrrolo[2,3-b]pyridine (*Tetrahedron Lett.* 1987, 1589) and 0.044 g of 10% palladium-on-charcoal in 15 mL of ethanol is stirred vigorously for 6 hours at room temperature and under 5 atmospheres of hydrogen. After this time, the suspension is filtered through Celite and the filtrate is concentrated under reduced pressure to give 0.24 g of the expected product in the form of a solid.
m.p.=193-195° C.
$^1$H NMR (DMSO-D$_6$), δ ppm: 7.5 (s, 1H); 6.93 (s, 1H); 5 (s, 2H); 3.91 (dxd, 2H); 2.95 (dxd, 2H); 2.49 (s, 3H).

1.3 N-[1-Acetyl-2,3-dihydro-1H-pyrrolo[2,3-b]pyrid-5-yl]-5-fluoro-1-(3-fluorobenzyl)-1H-indole-2-carboxamide (Compound 1)

To a solution, stirred at 20° C., of 0.28 g (0.97 mmol) of 5-fluoro-1-(3-fluorobenzyl)-1H-indole-2-carboxylic acid prepared in step 1.1, 186 mg (0.97 mmol) of N-(3-dimethylaminopropyl)-N'-ethylcarbodiimide hydrochloride (EDAC) and 131 mg (0.97 mmol) of 1-hydroxybenzotriazole (HOBT) in 15 mL of DMF are added 206 mg (1.17 mmol) of 1-acetyl-5-amino-2,3-dihydro-1H-pyrrolo[2,3-b]pyridine, prepared in step 1.2. The reaction mixture is stirred for 14 hours at 20° C. and then concentrated under reduced pressure. The resulting product is taken up in 100 mL of water. The suspension is then extracted with three times 30 mL of ethyl acetate. The combined organic phases are washed twice with 20 mL of water, dried over sodium sulfate and then concentrated under reduced pressure. The product obtained is purified by chromatography on a column of silica, eluting with a mixture of dichloromethane and methanol. 290 mg of the expected product are thus isolated.
m.p.=186-188° C.

$^1$H NMR (DMSO-D$_6$), δ ppm: 8.4 (s, 1H); 8.07 (s, 1H); 7.6 (m, 1H); 7.56 (m, 1H); 7.43 (s, 1H); 7.33 (m, 1H); 7.19 (m, 1H); 7.08 (m, 1H); 6.90 (m, 2H); 5.9 (s, 2H); 4.05 (dxd, 2H); 3.12 (dxd, 2H); 2.51 (s, 3H).

EXAMPLE 2

Compound 2

N-[1H-Pyrrolo[2,3-b]pyrid-5-yl]-5-fluoro-1-(3-fluorobenzyl)-1H-indole-2-carboxamide The process is performed according to a method similar to that described in Example 1.3 starting with 0.4 g (1.39 mmol) of 5-fluoro-1-(3-fluorobenzyl)-1H-indole-2-carboxylic acid prepared in step 1.1 and 0.22 g (1.67 mmol) of 5-amino-1H-pyrrolo[2,3-b]pyridine (*Synthesis* 2005, 15, 2503). 0.44 g of the expected product is thus isolated in the form of a white solid.
m.p.=266-267° C.
$^1$H NMR (DMSO-D$_6$), δ ppm: 11.55 (s, 1H); 10.37 (s, 1H); 8.45 (s, 1H); 8.31 (s, 1H); 7.6 (m, 1H); 7.53 (m, 1H); 7.45 (m, 2H); 7.3 (m, 1H); 7.17 (m, 1H); 7.05 (m, 1H); 6.92 (m, 2H); 6.45 (s, 1H); 5.9 (s, 2H).

EXAMPLE 3

Compound 3

N-[2,3-Dihydro-1H-pyrrolo[2,3-b]pyrid-5-yl]-5-fluoro-1-(3-fluorobenzyl)-1H-indole-2-carboxamide 0.62 mL (8.96 mmol) of acetyl chloride is added dropwise to a solution, stirred at 0° C., of 0.2 g (0.45 mmol) of compound 1, described in step 1.3, in 4 mL of methanol. The reactor is then closed and the mixture is stirred for 30 minutes at 20° C. and then for 16 hours at 70° C. After this time, the mixture is concentrated under reduced pressure and then taken up in 100 mL of ethyl acetate and 50 mL of saturated sodium hydrogen carbonate solution. The organic phase is separated out, washed with saturated sodium chloride solution, dried over sodium sulfate and then concentrated under reduced pressure. The resulting product is purified by chromatography on a column of silica, eluting with a mixture of dichloromethane and methanol. 108 mg of the expected product are thus isolated.
m.p.=230-232° C.
$^1$H NMR (DMSO-D$_6$), δ ppm: 10.19 (s, 1H); 7.98 (s, 1H); 7.6 (s, 1H); 7.55 (m, 2H); 7.34 (m, 2H); 7.19 (m, 1H); 7.09 (m, 1H); 6.9 (m, 2H); 6.22 (s, 1H); 5.9 (s, 2H); 3.5 (dxd, 2H); 3.01 (dxd, 2H).

EXAMPLE 4

Compound 4

N-[1H-Pyrrolo[3,2-b]pyrid-6-yl]-5-fluoro-1-(3-fluorobenzyl)-1H-indole-2-carboxamide The process is performed according to a method similar to that of Example 1.3 starting with 0.4 g (1.39 mmol) of 5-fluoro-1-(3-fluorobenzyl)-1H-indole-2-carboxylic acid prepared in step 1.1 and 0.22 g (1.67 mmol) of 6-amino-1H-pyrrolo[3,2-b]pyridine (Adesis). 0.22 g of the expected product is thus isolated in the form of a white solid.
m.p.=277-278° C.

¹H NMR (DMSO-D₆), δ ppm: 11.49 (s, 1H); 10.58 (s, 1H); 8.29 (m, 2H); 7.88 (s, 1H); 7.6 (m, 2H); 7.42 (s, 1H); 7.32 (m, 1H); 7.1 (m, 3H); 6.94 (m, 2H); 5.91 (s, 2H).

EXAMPLE 5

Compound 36

N-(1H-Pyrrolo[2,3-b]pyrid-5-yl)-5-trifluoromethyl-1-[(pyrid-4-yl)methyl)]-1H-indole-2-carboxamide 5.1 Ethyl 5-trifluoromethyl-1-[(pyrid-4-yl)methyl)]-1H-indole-2-carboxylate To a solution of 333 mg (1.29 mmol) of ethyl 5-trifluoromethyl-1H-indole-2-carboxylate in 5 mL of dry toluene, maintained under an inert atmosphere, are added, at room temperature, 283 mg (2.59 mmol) of 4-pyridylmethanol and 0.92 g (3.826 mmol) of (cyanomethylene)tributylphosphorane (CMBP). The reaction mixture is stirred at 110° C. for 15 hours and then concentrated to dryness. The crude reaction product is then purified by flash chromatography on a column of silica gel, eluting with a mixture of heptane and ethyl acetate to give 386 mg of the expected ethyl 5-trifluoromethyl-1-[(pyrid-4-yl)methyl)]-1H-indole-2-carboxylate in the form of a white solid.
¹H NMR (DMSO D₆), δ (ppm): 8.46 (d, 2H); 8.22 (s, 1H); 7.80 (d, 1H); 7.62 (d, 1H); 7.58 (s, 1H); 6.93 (d, 2H); 5.95 (s, 2H); 4.28 (q, 2H); 1.26 (t, 3H).
LC-MS: 349 [M+H]⁺

5.2 N-(1H-Pyrrolo[2,3-b]pyrid-5-yl)-5-trifluoromethyl-1-[(pyrid-4-yl)methyl)]-1H-indole-2-carboxamide To a solution of 150 mg (0.43 mmol) of ethyl 5-trifluoromethyl-1-[(pyrid-4-yl)methyl)]-1H-indole-2-carboxylate, obtained according to the protocol described in the preceding step, and 69 mg (0.52 mmol) of pyrrolo[2,3-b]pyrid-5-ylamine in 1.5 mL of dry toluene, maintained under an inert atmosphere, is added dropwise, at 0° C., 0.32 mL (0.645 mmol) of a solution of trimethylaluminium (2M/toluene). The reaction mixture is stirred at 110° C. for 15 hours and then concentrated under reduced pressure. The crude reaction product is then diluted with 50 mL of normal HCl solution and 100 mL of ethyl acetate. The organic phase is separated out, washed with 50 mL of saturated sodium chloride solution and then dried over sodium sulfate and concentrated under reduced pressure. The resulting product is purified by chromatography on a column of silica. 147 mg of the expected product are thus isolated.
¹H NMR (DMSO D₆), δ (ppm): 11.62 (s, 1H); 10.62 (s, 1H); 8.47 (d, 2H); 8.42 (s, 1H), 8.29-8.24 (m, 2H); 7.76 (d, 1H); 7.66 (s, 1H); 7.58 (dd, 1H); 7.46 (t, 1H); 7.03 (d, 2H); 6.45-6.43 (m, 1H); 6.00 (s, 2H).
LC-MS: 436 [M+H]⁺
m.p.=216-217° C.

EXAMPLE 6

Compound 5

N-(1H-Pyrrolo[2,3-b]pyrid-5-yl)-6-fluoro-1-[(3-methylphenyl)methyl]-1H-indole-2-carboxamide 6.1 Methyl 5-fluoro-1-[(3-methylphenyl)methyl]-1H-indole-2-carboxylate This compound is prepared, according to a process similar to that described in Example 5.1, by reacting 475 mg (2.459 mmol) of methyl 6-fluoro-1H-indole-2-carboxylate with 0.59 mL (4.918 mmol) of 3-methylphenylmethanol in the presence of 0.92 g (3.826 mmol) of (cyanomethylene)tributylphosphorane (CMBP). The resulting crude mixture is then purified by flash chromatography on a column of silica gel in a mixture of heptane and ethyl acetate to give 539 mg of the expected product in the form of a colourless oil.
¹H NMR (DMSO D₆), δ (ppm): 7.76 (dd, 1H); 7.46 (dd, 1H); 7.40 (s, 1H); 7.14 (t. 1 H); 7.06-6.99 (m, 2H); 6.89 (s, 1H); 6.75 (d, 1H); 5.78 (s, 2H); 3.81 (s, 3H); 2.21 (s, 3H).
LC-MS: 298 [M+H]⁺

6.2 N-(1H-Pyrrolo[2,3-b]pyrid-5-yl)-5-fluoro-1-[(3-methylphenyl)methyl]-1H-indole-2-carboxamide (Compound 5)

Compound 5 was prepared according to a process similar to that described in step 5.2 by reacting 200 mg (0.673 mmol) of methyl 5-fluoro-1-[(3-methylphenyl)methyl]-1H-indole-2-carboxylate prepared according to the protocol described in step 6.1 with 107 mg (0.807 mmol) of pyrrolo[2,3-b]pyrid-5-ylamine in the presence of 0.5 mL (1.01 mmol) of a solution of trimethylaluminium (2M/toluene). The product is collected by filtration, to give 107 mg of the expected product.
¹H NMR (DMSO D₆), δ (ppm): 11.61 (s, 1H); 10.45 (s, 1H); 8.44 (d, 1H); 8.32 (d, 1H); 7.76 (dd, 1H); 7.47-7.42 (m, 3H); 7.14 (t, 1H); 7.05-6.98 (m, 3H); 6.86 (d, 1H); 6.45 (m, 1H); 5.82 (s, 2H); 2.20 (s, 3H).
m.p.=310-311° C.

EXAMPLE 7

Compound 30

N-(1H-Pyrrolo[2,3-b]pyrid-5-yl)-5-trifluoromethyl-1-[(thiazol-2-yl)methyl]-1H-pyrrolo[2,3-b]pyridine-2-carboxamide 7.1 Ethyl 5-trifluoromethyl-1-[(thiazol-2-yl)methyl]-1H-pyrrolo[2,3-b]pyridine-2-carboxylate This compound was prepared according to a process similar to that described in step 5.1. by reacting 390 mg (1.51 mmol) of ethyl 5-trifluoromethyl-1H-pyrrolo[2,3-b]pyridine-2-carboxylate (WO2008/107543) with 348 mg (3.02 mmol) of thiazol-2-ylmethanol in the presence of 0.92 g (3.826 mmol) of (cyanomethylene)-tributylphosphorane (CMBP). The reaction mixture is then purified by flash chromatography on a column of silica gel in a mixture of heptane and ethyl acetate to give 446 mg of the expected product in the form of an oil.
¹H NMR (DMSO D₆), δ (ppm): 8.84 (s, 1H); 8.69 (s, 1H); 7.67 (d, 1H), 7.60 (d, 1H), 7.54 (s, 1H); 6.22 (s, 2H); 4.32 (q, 2H); 1.28 (t, 3H).
LC-MS: 356 [M+H]⁺

7.2 N-(1H-Pyrrolo[2,3-b]pyrid-5-yl)-5-trifluoromethyl-1-[(thiazol-2-yl)methyl]-1H-pyrrolo[2,3-b]pyridine-2-carboxamide (Compound 30)

Compound 30 was prepared according to a process similar to that described in step 5.1 by reacting 186 mg (0.523 mmol) of ethyl 5-trifluoromethyl-1-[(thiazol-2-yl)methyl]-1H-pyrrolo[2,3-b]pyridine-2-carboxylate prepared according to the protocol described in step 7.1 with 84 mg (0.628 mmol) of pyrrolo[2,3-b]pyrid-5-ylamine in the presence of 0.39 mL (0.785 mmol) of a solution of trimethylaluminium (2M/toluene). The product is collected by filtration, to give 144 mg of expected product.

$^1$H NMR (DMSO D$_6$), δ (ppm): 11.70 (s, 1H); 10.76 (s, 1H); 8.81-8.76 (m, 2H); 8.47 (s, 1H); 8.35 (s, 1H); 7.67-7.58 (m, 3H); 7.50-7.49 (m, 1H); 6.49-6.47 (m, 1H); 6.29 (s, 2H).

LC-MS: 443 [M+H]$^+$ m.p.=274-275° C.

EXAMPLE 8

Compound 37

N-(1H-Pyrrolo[2,3-b]pyrid-5-yl)-6-trifluoromethyl-1-[(pyrid-4-yl)methyl)]-1H-indole-2-carboxamide

8.1 Methyl 6-trifluoromethyl-1-[(pyrid-4-yl)methyl)]-1H-indole-2-carboxylate This compound was prepared according to a process similar to that described in step 5.1 by reacting 500 mg (2.056 mmol) of methyl 6-trifluoromethyl-1H-indole-2-carboxylate with 449 mg (4.11 mmol) of 4-pyridylmethanol in the presence of 0.92 g (3.826 mmol) of (cyanomethylene)tributylphosphorane (CMBP). The crude reaction product is then purified by flash chromatography on a column of silica gel in a mixture of heptane and ethyl acetate to give 407 mg of the expected product in the form of a beige-coloured solid.

$^1$H NMR (DMSO D$_6$), δ (ppm): 8.46 (d, 2H); 8.09 (s, 1H); 7.99 (d, 1H); 7.54 (s, 1H), 7.46 (d, 1 H); 6.90 (d, 2H); 6.00 (s, 2H); 3.82 (s, 3H).

LC-MS: 335 [M+H]$^+$

8.2 N-(1H-Pyrrolo[2,3-b]pyrid-5-yl)-6-trifluoromethyl-1-[(pyrid-4-yl)methyl)]-1H-indole-2-carboxamide (Compound 37)

Compound 37 was prepared according to a process similar to that described in step 5.2 by reacting 150 mg (0.449 mmol) of methyl 6-trifluoromethyl-1-[(pyrid-4-yl)methyl)]-1H-indole-2-carboxylate prepared in the preceding step with 72 mg (0.538 mmol) of pyrrolo[2,3-b]pyrid-5-ylamine in the presence of 0.34 mL (0.674 mmol) of a solution of trimethylaluminium (2M/toluene). The product is collected by filtration, to give 99 mg of expected product.

$^1$H NMR (DMSO D$_6$), δ (ppm): 11.71 (s, 1H); 10.72 (s, 1H); 8.77 (d, 2H); 8.45 (d, 1H); 8.30 (d, 1H); 8.12 (s, 1H); 8.06 (d, 1H); 7.76 (s, 1H); 7.52-7.47 (m, 4H); 6.45 (m, 1H); 6.23 (s, 2H).

LC-MS: 436 [M+H]$^+$ m.p.=311-313° C.

EXAMPLE 9

Compound 6

N-(1H-Pyrrolo[2,3-b]pyrid-5-yl)-6-trimethylsilyl-1-[[(3-trifluoromethyl)phenyl]-methyl]-1H-indole-2-carboxamide

9.1 Ethyl 2-azido-3-(4-trimethylsilylphenyl)propenoate 1.26 g (54.96 mmol) of sodium and 30 mL of anhydrous ethanol are introduced into a 100 mL round-bottomed flask, equipped with a magnetic stirrer and maintained under a nitrogen atmosphere. The reaction mixture is stirred at room temperature until a homogeneous solution is obtained. To this solution, cooled to −10° C., is added dropwise a solution containing 16.83 mL (54.96 mmol) of ethyl azidoacetate (34% in CH$_2$Cl$_2$) and 5 g (27.48 mmol) of 4-trimethylsilyl-benzaldehyde in 5 mL of ethanol. The reaction mixture is then stirred at 0° C. for 4 hours. The reaction medium is hydrolysed by adding, with vigorous stirring, 100 mL of ammonium chloride solution (30% aqueous). The product is extracted with three times 50 mL of ethyl acetate. The combined organic phases are washed with twice 20 mL of water, dried over sodium sulfate and concentrated under reduced pressure. The resulting oil is purified by chromatography on a column of silica gel, eluting with a mixture of heptane and dichloromethane. 4.96 g of the expected product are isolated in the form of a yellow oil.

$^1$H NMR (DMSO D$_6$), δ (ppm): 7.6 (d, 2H); 7.35 (d, 2H); 6.7 (s, 1H); 4.1 (q, 2H); 1.1 (t, 3H); 0 (s, 9H).

9.2 Ethyl 6-trimethylsilyl-1H-indole-2-carboxylate

To a solution of 1.0 g (3.14 mmol) of ethyl 2-azido-3-(4-trimethylsilylphenyl)propenoate obtained in the preceding step, in 20 mL of dry toluene, maintained under an inert atmosphere, is added 0.17 g (0.16 mmol) of dirhodium (II) heptafluorobutyrate dimer complex. The reaction mixture is then stirred for 12 hours at 70° C. After cooling to room temperature, the reaction mixture is filtered through silica gel, eluting with ethyl acetate. The filtrate is then concentrated under reduced pressure. The residue is purified by chromatography on a column of silica gel, eluting with a mixture of heptane and dichloromethane. 0.61 g of the expected product is isolated in the form of a beige-coloured powder.

m.p.=127-129° C.

$^1$H NMR (DMSO D$_6$), δ (ppm): 11.7 (s, 1H); 7.41 (dd, 1H); 7.39 (d, 1H); 6.97 (dd, 1H); 6.88 (d, 1H); 4.1 (q, 2H); 1.1 (t, 3H); 0.0 (s, 9H).

9.3 Ethyl 6-trimethylsilyl-1-[[(3-trifluoromethyl)phenyl]methyl]-1H-indole-2-carboxylate (Compound IIb)

This compound was prepared according to a process similar to that described in step 5.1 by reacting 500 mg (1.913 mmol) of ethyl 6-trimethylsilyl-1H-indole-2-carboxylate with 0.52 mL (3.826 mmol) of 3-(trifluoromethyl)phenyl-methanol in the presence of 0.92 g (3.826 mmol) of (cyanomethylene)tributylphosphorane (CMBP). The crude reaction product is then purified by flash chromatography on a column of silica gel in a mixture of heptane and ethyl acetate to give 720 mg of the expected product.

$^1$H NMR (DMSO D$_6$), δ (ppm): 7.49-7.45 (m, 2H); 7.36-7.33 (m, 2H); 7.25 (t, 1H); 7.12 (s, 1H); 7.04-7.00 (m, 2H); 5.73 (s, 2H); 4.04 (q, 2H); 1.03 (t, 3H); 0.00 (s, 9H).

LC-MS: 420 [M+H]$^+$

9.4 N-(1H-Pyrrolo[2,3-b]pyrid-5-yl)-6-trimethylsilyl-1-[[(3-trifluoromethyl)phenyl]-methyl]-1H-indole-2-carboxamide (Compound 6)

Compound 6 was prepared according to a process similar to that described in step 5.2 by reacting 200 mg (0.477 mmol) of ethyl 6-trimethylsilyl-1-[[(3-trifluoromethyl)phenyl]-methyl]-1H-indole-2-carboxylate prepared according to the protocol described in the preceding step with 76 mg (0.572 mmol) of pyrrolo[2,3-b]pyrid-5-ylamine in the presence of 0.36 mL (0.716 mmol) of a solution of trimethylaluminium (2M/toluene). The product is isolated by purification by flash chromatography on a column of silica gel in a mixture of heptane and ethyl acetate. 163 mg of expected product are obtained.

$^1$H NMR (DMSO D$_6$), δ (ppm): 11.60 (s, 1H); 10.49 (s, 1H); 8.45 (d, 1H); 8.32 (d, 1H); 7.74-7.68 (m, 3H); 7.51-7.43 (m, 5H); 7.28 (d, 1H); 7.45-7.44 (m, 1H); 6.01 (s, 2H); 0.25 (s, 9H).

LC-MS: 507 [M+H]$^+$ m.p.=251-252° C.

EXAMPLE 10

Compound 7

N-(1H-Pyrrolo[2,3-b]pyrid-5-yl)-5-trimethylsilyl-1-[[(3-trifluoromethyl)phenyl]-methyl]-1H-indole-2-carboxamide

10.1 1-Bromo-3-trimethylsilylbenzene

To a solution of 10 g (42.39 mmol) of 1,3-dibromobenzene in 80 mL of anhydrous Et$_2$O, cooled to −78° C. and maintained under a nitrogen atmosphere, are added dropwise with stirring, over 30 minutes, 26.49 mL (42.39 mmol) of a solution of BuLi (1.5M/hexane). After stirring for a further 30 minutes at −78° C., 5.96 mL (46.63 mmol) of TMSCl are added dropwise to the reaction mixture. Stirring is maintained at this temperature for 90 minutes and the reaction mixture is then hydrolysed by adding 15 mL of water. The product is extracted with ethyl acetate (3×50 mL). The combined organic phases are washed with saturated aqueous NaCl solution (2×25 mL), dried over Na$_2$SO$_4$, filtered and evaporated under reduced pressure. The crude reaction product is purified by chromatography on a column of silica gel, eluting with heptane, to give 9.3 g of the expected 1-bromo-3-trimethylsilylbenzene, in the form of a colourless oil.

$^1$H NMR (DMSO D$_6$), δ (ppm): 5.75 (s, 1H), 7.46 (m, 1H), 7.4 (m, 1H), 7.22 (t, 1H), 0.2 (s, 9H).

10.2 3-Trimethylsilylbenzaldehyde

To a solution of 5 g (21.89 mmol) of 1-bromo-3-trimethylsilylbenzene prepared according to the protocol described in the preceding step, in 40 mL of anhydrous Et$_2$O, cooled to 0° C. and maintained under a nitrogen atmosphere, are added dropwise, with stirring and over 30 minutes, 16.36 mL (26.18 mmol) of BuLi (1.6M/hexane). Stirring is continued at 0° C. for a further 30 minutes, and the mixture is then maintained at room temperature for 90 minutes. 2.69 mL (34.91 mmol) of DMF, diluted with 17 mL of anhydrous Et$_2$O, are then introduced into the reaction mixture. After stirring for 3 hours at room temperature, the reaction mixture is hydrolysed at 0° C. by successive addition of 10 mL of concentrated HCl solution and 100 mL of water. The product is extracted with 3×50 mL of CH$_2$Cl$_2$. The combined organic phases are washed with 100 mL of water, dried over Na$_2$SO$_4$, filtered and evaporated under reduced pressure. The crude reaction product is purified by flash chromatography on a column of silica gel, eluting with a gradient of from 10 to 20% of CH$_2$Cl$_2$ in heptane to give 1.82 g of the expected 3-trimethylsilylbenzaldehyde in the form of a yellow oil.

$^1$H NMR (DMSO D$_6$), δ (ppm): 10.01 (s, 1H); 8.0 (s, 1H); 7.85 (d, 1H); 7.8 (d, 1H); 7.5 (dd, 1H) 0.3 (s, 9H)

10.3 Ethyl 2-azido-3-(3-trimethylsilylphenyl)propenoate

To a solution of 2 g (87.5 mmol) of sodium in 30 mL of anhydrous EtOH, maintained under a nitrogen atmosphere and cooled to −10° C., is added, dropwise, a mixture of 31.4 mL (87.5 mmol) of ethyl azidoacetate (at 34% in CH$_2$Cl$_2$) and 3.9 g (21.87 mmol) of 3-trimethylsilylbenzaldehyde prepared according to the procedure described in the preceding step, diluted with 3 mL of EtOH. The reaction mixture is stirred at 0° C. for 4 hours. It is then hydrolysed by adding, with vigorous stirring, 100 mL of aqueous NH$_4$Cl solution (30%). The aqueous phase is extracted with 3×50 mL of EtOAc. The combined organic phases are washed with water, dried over Na$_2$SO$_4$ and concentrated under reduced pressure. The crude reaction product is purified by chromatography on a column of silica gel, eluting with an isocratic mixture of heptane and CH$_2$Cl$_2$ (80/20). 1.7 g of the expected ethyl 2-azido-3-(3-trimethylsilylphenyl)propenoate are thus isolated in the form of a yellow oil.

$^1$H NMR (DMSO D$_6$), δ (ppm): 7.9 (d, 1H); 7.8 (s, 1H); 7.4 (d, 1H); 7.3 (dd, 1H); 6.9 (s, 1H); 4.2 (q, 2H); 1.2 (t, 3H); 0.15 (s, 9H)

MS: [MH]$^+$=289

10.4 Ethyl 5-trimethylsilyl-1H-indole-2-carboxylate

To a solution of 1.7 g (5.90 mmol) of ethyl 2-azido-3-(3-trimethylsilylphenyl)propenoate prepared according to the procedure described in the preceding step, in 25 mL of dry toluene, maintained under an inert atmosphere, is added 0.62 g (0.59 mmol) of dirhodium (II) heptafluorobutyrate dimer complex. The reaction mixture is stirred for 7 hours at 40° C. A second portion of 0.62 g (0.59 mmol) of dirhodium (II) heptafluorobutyrate dimer complex is added to the reaction mixture while maintaining the stirring and heating at 40° C. for a further 1 hour. After cooling to room temperature, the reaction mixture is filtered through silica gel, eluting with toluene. The filtrate is then concentrated under reduced pressure. The greenish solid obtained is triturated several times in a minimum amount of heptane, until a white powder is obtained. This powder is dried under reduced pressure to give 0.87 g of the expected ethyl 5-trimethylsilyl-1H-indole-2-carboxylate in the form of a white powder.

m.p.=114-115° C.

$^1$H NMR (DMSO D$_6$), δ (ppm): 7.7 (s, 1H); 7.35 (d, 1H); 7.25 (d, 1H); 7.0 (s, 1H); 4.2 (q, 2H); 1.2 (t, 3H); 0.15 (s, 9H)

LC-MS: [MH]$^-$=260

10.5 Ethyl 5-trimethylsilyl-1-[[(3-trifluoromethyl)phenyl]methyl]-1H-indole-2-carboxylate (Compound IIa)

This compound was prepared according to a process similar to that described in step 5.1 by reacting 0.49 g (1.87 mmol) of ethyl 5-trimethylsilyl-1H-indole-2-carboxylate with 0.51 mL (3.749 mmol) of 3-(trifluoromethyl)phenylmethanol in the presence of 0.9 g (3.749 mmol) of (cyanomethylene)tributylphosphorane (CMBP). The crude reaction product is then purified by flash chromatography on a column of silica gel in a mixture of heptane and ethyl acetate to give 730 mg of the expected product.

$^1$H NMR (DMSO D$_6$), δ (ppm): 7.90 (s, 1H); 7.62-7.57 (m, 2H); 7.51-7.43 (m, 3H); 7.40 (s, 1H); 7.17 (d, 1H); 5.92 (s, 2H); 4.28 (q, 2H); 1.26 (t, 3H); 0.27 (s, 9H).

LC-MS: 420 ([M+H]$^+$

10.6 N-(1H-Pyrrolo[2,3-b]pyrid-5-yl)-5-trimethylsilyl-1-[[(3-trifluoromethyl)phenyl]-methyl]-1H-indole-2-carboxamide (Compound 7)

Compound 7 was prepared according to a process similar to that described in step 5.2 by reacting 200 mg (0.477 mmol)

of ethyl 5-trimethylsilyl-1-[[(3-trifluoromethyl)phenyl]-methyl]-1H-indole-2-carboxylate, prepared according to the protocol described in step 10.5, with 76 mg (0.572 mmol) of pyrrolo[2,3-b]pyrid-5-ylamine in the presence of 0.36 mL (0.716 mmol) of a solution of trimethylaluminium (2M/toluene). The product is collected by filtration, to give 107 mg of the expected product.
$^1$H NMR (DMSO D$_6$), δ (ppm): 11.51 (s, 1H); 10.38 (s, 1H); 8.34 (d, 1H); 8.21 (d, 1H); 7.80 (s, 1H); 7.51-7.41 (m, 3H); 7.38-7.30 (m, 4H); 7.26-7.23 (m, 1H); 6.36-6.34 (m, 1H); 5.87 (s, 2H); 0.19 (s, 9H).
LC-MS: 507 ([M+H]$^+$
m.p.=199-200° C.

EXAMPLE 11

Compound 42

N-(2-Oxo-2,3-dihydro-1H-pyrrolo[2,3-b]pyrid-5-yl)-5-fluoro-1-[(3-fluorophenyl)-methyl]-1H-indole-2-carboxamide

11.1 5-Fluoro-1-[(3-fluorophenyl)methyl]-1H-indole-2-carboxylic acid chloride This product is prepared by refluxing for 3 hours a solution of 10 g (34.81 mmol) of 5-fluoro-1-[(3-fluorophenyl)methyl]-1H-indole-2-carboxylic acid, prepared in step 1.1, and 25.4 mL (0.348 mol) of sulfonyl chloride in 174 mL of toluene. After this time, the reaction mixture is concentrated under reduced pressure. The resulting mixture is taken up twice successively in 100 mL of toluene and then concentrated under reduced pressure. The product is used in the rest of the synthesis without a further purification step.

11.2 N-(2-Oxo-2,3-dihydro-1H-pyrrolo[2,3-b]pyrid-5-yl)-5-fluoro-1-[(3-fluorophenyl)-methyl]-1H-indole-2-carboxamide (Compound 42)

A solution of 1.3 g (4.25 mmol) of 5-fluoro-1-[(3-fluorophenyl)methyl]-1H-indole-2-carboxylic acid chloride, prepared in the preceding step, 2.1 mL (14.9 mmol) of triethylamine and 1.45 (4.68 mmol) of 5-amino-2-oxo-2,3-dihydro-1H-pyrrolo[2,3-b]pyridine dihydrobromide (US 2005/256 125) in 42.5 mL of dichloromethane is stirred for 24 hours at room temperature. After this time, the mixture is poured into 200 mL of water. 100 mL of dichloromethane are added and the organic phase is then separated out, washed with twice 50 mL of water and concentrated under reduced pressure. The product obtained is purified by chromatography on a column of silica, eluting with a mixture of ethyl acetate and dichloromethane. The product thus purified is taken up in 100 mL of hot methanol, and the resulting suspension is filtered. The filtrate is concentrated under reduced pressure, thus allowing 0.4 g of the expected product to be isolated.
m.p.=272-275° C.
$^1$H NMR (DMSO-D$_6$), δ ppm: 10.94 (s, 1H); 10.49 (s, 1H); 8.32 (s, 1H); 7.95 (s, 1H); 7.6 (m, 1H); 7.55 (m, 1H); 7.41 (s, 1H); 7.31 (m, 1H); 7.17 (m, 1H); 7.05 (m, 1H); 6.9 (m, 2H); 5.9 (s, 2H); 3.58 (s, 2H).

EXAMPLE 12

Compound 19

N-(1H-Pyrrolo[2,3-b]pyrid-5-yl)-5-trifluoromethyl-1-[(3-methylphenyl)methyl]-1H-indole-2-carboxamide This compound was prepared according to a protocol similar to that described in Example 5.
m.p.: 311-312° C.
$^1$H NMR (DMSO D$_6$), δ (ppm): 11.6 (s, 1H); 10.6 (s, 1H); 8.5 (s, 1H); 8.35 (s, 1H); 8.2 (s, 1H); 7.8 (d, 1H); 7.55 (m, 2H); 7.5 (m, 1H); 7.15 (t, 1H); 7.0 (m, 2H); 6.9 (d, 1H); 6.5 (d, 1H); 5.9 (s, 2H); 2.2 (s, 3H).

EXAMPLE 13

Compound 20

N-(1H-Pyrrolo[2,3-b]pyrid-5-yl)-6-trifluoromethyl-1-[(3-methylphenyl)methyl]-1H-indole-2-carboxamide This compound was prepared according to a protocol similar to that described in Example 5.
m.p.: 278-279° C.
$^1$H NMR (DMSO D$_6$), δ (ppm): 11.7 (s, 1H); 10.6 (s, 1H); 8.5 (s, 1H); 8.4 (s, 1H); 8.05 (s, 1H); 7.95 (d, 1H); 7.50 (m, 2H); 7.45 (d, 1H); 7.15 (t, 1H); 7.05 (d, 1H); 7.0 (s, 1H); 6.9 (d, 1H); 6.5 (s, 1H); 5.95 (s, 2H); 2.2 (s, 3H).

EXAMPLE 14

Compound 21

N-(1H-Pyrrolo[2,3-b]pyrid-5-yl)-5-trimethylsilyl-1-[(3-methylphenyl)methyl]-1H-indole-2-carboxamide

14.1 Ethyl 5-trimethylsilyl-1-[(3-methylphenyl)methyl]-1H-indole-2-carboxylate (Compound IIc)

This compound was prepared according to a process similar to that described in step 5.1 by reacting ethyl 5-trimethylsilyl-1H-indole-2-carboxylate prepared according to the process described in step 10.4 with (3-methylphenyl)methanol in the presence of (cyanomethylene)tributylphosphorane (CMBP). The crude reaction product is then purified by flash chromatography on a column of silica gel to give the expected product.
$^1$H NMR (DMSO D$_6$), δ (ppm): 7.87 (s, 1H); 7.55 (d, 1H); 7.43 (d, 1H); 7.36 (s, 1H); 7.13 (t, 1H); 7.01 (d, 1H); 6.91 (s, 1H); 6.73 (d, 1H); 5.80 (s, 2H); 4.29 (q, 2H); 2.21 (s, 3H); 1.29 (t, 3H); 0.26 (s, 9H).

14.2 N-(1H-Pyrrolo[2,3-b]pyrid-5-yl)-5-trimethylsilyl-1-[(3-methylphenyl)methyl]-1H-indole-2-carboxamide (Compound 21)

This compound was prepared according to a protocol similar to that described in Example 5.
m.p.: 327-328° C.
$^1$H NMR (DMSO D$_6$), δ (ppm): 11.6 (s, 1H); 10.4 (s, 1H); 8.5 (s, 1H); 8.3 (s, 1H); 7.9 (s, 1H); 7.55 (d, 1H); 7.45 (m, 1H); 7.4 (m, 2H); 7.15 (t, 1H); 7.0 (m, 2H); 6.9 (d, 1H); 6.45 (d, 1H); 5.85 (s, 2H); 2.2 (s, 3H); 0.3 (s, 9H).

EXAMPLE 15

Compound 22

N-(1H-Pyrrolo[2,3-b]pyrid-5-yl)-5-trifluoromethyl-1-[(3-methylphenyl)methyl]-1H-pyrrolo[2,3-b]pyridine-2-carboxamide This compound was prepared according to a protocol similar to that described in Example 5.
m.p.: 305-306° C.

¹H NMR (DMSO D₆), δ (ppm): 11.6 (s, 1H); 10.6 (s, 1H); 8.8 (s, 1H); 8.7 (s, 1H); 8.4 (s, 1H); 8.3 (s, 1H); 7.55 (s, 1H); 7.5 (m, 1H); 7.1 (t, 1H); 7.0 (m, 2H); 6.9 (d, 1H); 6.5 (d, 1H); 6.0 (s, 2H); 2.2 (s, 3H).

EXAMPLE 16

Compound 23

N-(1H-Pyrrolo[2,3-b]pyrid-5-yl)-6-trimethylsilyl-1-[(3-methylphenyl)methyl]-1H-indole-2-carboxamide

16.1 Ethyl 6-trimethylsilyl-1-[(3-methylphenyl)methyl]-1H-indole-2-carboxylate (Compound IId)

This compound was prepared according to a process similar to that described in step 5.1 by reacting ethyl 6-trimethylsilyl-1H-indole-2-carboxylate prepared according to the process described in step 9.2 with (3-methylphenyl)methanol in the presence of (cyanomethylene)tributylphosphorane (CMBP). The crude reaction product is then purified by flash chromatography on a column of silica gel to give the expected product.

¹H NMR (DMSO D₆), δ (ppm): 7.71-7.68 (m, 2H); 7.33 (s, 1H); 7.24-7.21 (m, 1 H); 7.14-7.11 (m, 2H); 7.09-7.0 (m, 1H); 6.81-6.79 (m, 1H); 5.85 (s, 2H); 4.30 (q, 2 H); 2.21 (s, 3H); 1.17 (t, 3H), 0.25 (s, 9H).

16.2 N-(1H-Pyrrolo[2,3-b]pyrid-5-yl)-6-trimethylsilyl-1-[(3-methylphenyl)methyl]-1H-indole-2-carboxamide (Compound 23)

This compound was prepared according to a protocol similar to that described in Example 5.
m.p.: 202-203° C.
¹H NMR (DMSO D₆), δ (ppm): 11.6 (s, 1H); 10.45 (s, 1H); 8.5 (s, 1H); 8.35 (s, 1H); 7.7 (m, 2H); 7.5 (d, 1H); 7.35 (m, 1H); 7.25 (d, 1H); 7.15 (t, 1H); 7.1 (s, 1H); 7.0 (d, 1H); 6.95 (d, 1H); 6.45 (s, 1H); 5.9 (s, 2H); 2.2 (s, 3H); 0.25 (s, 9H).

EXAMPLE 17

Compound 24

N-(1H-Pyrrolo[2,3-b]pyrid-5-yl)-5-trifluoromethyl-1-[[(3-trifluoromethyl)phenyl]-methyl]-1H-indole-2-carboxamide This compound was prepared according to a protocol similar to that described in Example 5.
m.p.: 247-248° C.
¹H NMR (DMSO D₆), δ (ppm): 11.65 (s, 1H); 10.7 (s, 1H); 8.5 (s, 1H); 8.35 (s, 1H); 8.25 (s, 1H); 7.9 (d, 1H); 7.7-7.5 (m, 6H); 7.4 (m, 1H); 6.5 (m, 1H); 6.1 (s, 2H).

EXAMPLE 18

Compound 25

N-(1H-Pyrrolo[2,3-b]pyrid-5-yl)-6-trifluoromethyl-1-[[(3-trifluoromethyl)phenyl]-methyl]-1H-indole-2-carboxamide This compound was prepared according to a protocol similar to that described in Example 5.
m.p.: 334-335° C.
¹H NMR (DMSO D₆), δ (ppm): 11.6 (s, 1H); 10.6 (s, 1H); 8.49 (s, 1H); 8.30 (s, 1H); 8.1 (s, 1H); 8.0 (d, 1H); 7.6-7.4 (m, 6H); 7.35 (m, 1H); 6.45 (m, 1H); 6.1 (s, 2H).

EXAMPLE 19

Compound 26

N-(1H-Pyrrolo[2,3-b]pyrid-5-yl)-5-trifluoromethyl-1-[[(3-trifluoromethyl)phenyl]-methyl]-1H-pyrrolo[2,3-b]pyridine-2-carboxamide This compound was prepared according to a protocol similar to that described in Example 5.
m.p.: 273-274° C.
¹H NMR (DMSO D₆), δ (ppm): 11.65 (s, 1H); 10.7 (s, 1H); 8.85 (s, 1H); 8.75 (s, 1H); 8.45 (s, 1H); 8.3 (s, 1H); 7.65-7.35 (m, 6H); 6.5 (m, 1H); 6.1 (s, 2H).

EXAMPLE 20

Compound 27

N-(1H-Pyrrolo[2,3-b]pyrid-5-yl)-6-fluoro-1-[[(3-trifluoromethyl)phenyl]methyl]-1H-indole-2-carboxamide This compound was prepared according to a protocol similar to that described in Example 5.
m.p.: 288-289° C.
¹H NMR (DMSO D₆), δ (ppm): 11.6 (s, 1H); 10.45 (s, 1H); 8.45 (d, 1H); 8.25 (d, 1H); 7.8 (m, 1H); 7.65-7.45 (m, 6H); 7.35 (m, 1H); 7.05 (m, 1H); 6.45 (m, 1H); 5.95 (s, 2H).

EXAMPLE 21

Compound 31

N-(1H-Pyrrolo[2,3-b]pyrid-5-yl)-6-trimethylsilyl-1-[(thiazol-2-yl)methyl]-1H-indole-2-carboxamide

21.1 Ethyl 6-trimethylsilyl-1-[(thiazol-2-yl)methyl]-1H-indole-2-carboxylate (Compound IIf)

This compound was prepared according to a process similar to that described in step 5.1 by reacting ethyl 6-trimethylsilyl-1H-indole-2-carboxylate prepared according to the process described in step 9.2 with (thienyl-2-yl)methanol in the presence of (cyanomethylene)tributylphosphorane (CMBP). The crude reaction product is then purified by flash chromatography on a column of silica gel to give the expected product.

¹H NMR (DMSO D₆), δ (ppm): 7.76 (s, 1H); 7.65-7.61 (m, 2H); 7.52 (d, 1H); 7.28 (s, 1H); 7.22 (s, 1H); 6.09 (s, 2H); 4.23 (q, 2H); 1.22 (t, 3H); 0.2 (s, 9H).

21.2 N-(1H-Pyrrolo[2,3-b]pyrid-5-yl)-6-trimethylsilyl-1-[(thiazol-2-yl)methyl]-1H-indole-2-carboxamide (Compound 31)

This compound was prepared according to a protocol similar to that described in Example 5.
m.p.: 269-270° C.
¹H NMR (DMSO D₆), δ (ppm): 11.6 (s, 1H); 10.45 (s, 1H); 8.45 (d, 1H); 8.35 (d, 1H); 7.85 (s, 1H); 7.75 (m, 2H); 7.6 (d, 1H); 7.45 (m, 2H); 7.3 (d, 1H); 6.45 (m, 1H); 6.2 (s, 2H); 0.3 (s, 9H).

EXAMPLE 22

Compound 41

N-(1H-Pyrrolo[2,3-b]pyrid-5-yl)-5-trifluoromethyl-1-[(pyrid-4-yl)methyl)]-1H-pyrrolo[2,3-b]pyridine-2-carboxamide This compound was prepared according to a protocol similar to that described in Example 5.

m.p.: 296-298° C.

$^1$H NMR (DMSO D$_6$), δ (ppm): 8.8 (d, 2H); 8.6 (d, 2H); 8.4 (s, 1H); 8.30 (s, 1H); 7.75 (s, 1H); 7.5 (m, 1H); 7.35 (d, 2H); 6.45 (m, 1H); 6.1 (s, 2H).

EXAMPLE 23

Compound 8

N-(1H-Pyrrolo[2,3-c]pyrid-5-yl)-5-fluoro-1-[(3-fluorophenyl]methyl]-1H-indole-2-carboxamide This compound was prepared according to a protocol similar to that described in Example 5.

m.p.: 203-204° C.

$^1$H NMR (DMSO D$_6$), δ (ppm): 11.5 (s, 1H); 10.59 (s, 1H); 8.57 (s, 1H); 8.25 (s, 1H); 7.52 (m, 4H); 7.31 (m, 1H); 7.15 (m, 1H); 7.03 (m, 1H); 6.92 (m, 2H); 6.5 (m, 1H); 5.92 (s, 2H).

EXAMPLE 24

Compound 9

N-(1H-Pyrrolo[2,3-b]pyrid-5-yl)-5-trifluoromethyl-1-[(3-fluorophenyl)methyl]-1H-pyrrolo[2,3-b]pyridine-2-carboxamide This compound was prepared according to a method similar to that of Example 1.3.

m.p.: 319-320° C.

$^1$H NMR (DMSO D$_6$), δ (ppm): 11.65 (s, 1H); 10.7 (s, 1H); 8.82 (s, 1H); 8.73 (s, 1H); 8.42 (s, 1H); 8.3 (s, 1H); 7.6 (s, 1H); 7.5 (s, 1H); 7.31 (m, 1H); 7.09 (m, 1H); 6.98 (m, 2H); 6.49 (m, 1H); 6.01 (s, 2H).

EXAMPLE 25

Compound 10

N-(7-Oxy-1H-pyrrolo[2,3-b]pyrid-5-yl)-5-fluoro-1-[(3-fluorophenyl)methyl]-1H-indole-2-carboxamide This compound was prepared by stirring for 30 hours at 20° C. a mixture of 0.5 g (1.24 mol) of compound 2 (Example 2) in the presence of 0.66 g (2.74 mmol) of meta-chloroperbenzoic acid in 130 mL of dichloromethane. After this time, the mixture is poured into 200 mL of water and 200 mL of dichloromethane. The organic phase is separated out, washed once with 100 mL of saturated sodium hydrogen carbonate solution, twice with 100 mL of water, dried over magnesium sulfate and then concentrated under reduced pressure. The resulting product is purified by chromatography on a column of silica, to give 0.13 g of expected product.

m.p.: 260-263° C.

$^1$H NMR (DMSO D$_6$), δ (ppm): 12.41 (s, 1H); 10.6 (s, 1H); 8.59 (s, 1H); 8.03 (s, 1H); 7.6 (m, 2H); 7.42 (m, 2H); 7.31 (m, 1H); 7.19 (m, 1H); 7.05 (m, 1H); 6.93 (m, 2H); 6.59 (s, 1H); 5.89 (s, 2H).

EXAMPLE 26

Compound 12

N-(1-Methyl-1H-pyrrolo[2,3-b]pyrid-5-yl)-5-fluoro-1-[(3-fluorophenyl)methyl]-1H-indole-2-carboxamide

26.1 5-Fluoro-1-[(3-fluorophenyl)methyl]-1H-indole-2-carboxamide

To a suspension, stirred at 20° C., of 2 g (6.96 mmol) of 5-fluoro-1-[(3-fluorophenyl)methyl]-1H-indole-2-carboxylic acid, prepared in step 1.1, in 80 mL of dry toluene are added 5.08 mL (69.62 mmol) of thionyl chloride. The reaction mixture is stirred for 2 hours at reflux and then concentrated under reduced pressure. The resulting product is taken up in 10 mL of dichloromethane and this solution is poured, dropwise, into a solution of 9.12 mL (69.62 mmol) of 30% aqueous ammonia in water. The reaction mixture is stirred for 14 hours at 20° C. After this time, a solid is collected by filtration and triturated in 50 mL of diisopropyl ether. After filtering and drying under reduced pressure, 0.58 g of expected product is collected.

$^1$H NMR (DMSO-D$_6$), δ ppm: 8.11 (broad peak, 1H); 7.5 (m, 3H); 7.32 (m, 1H); 7.25 (s, 1H); 7.09 (m, 2H); 6.89 (m, 2H); 5.91 (s, 2H).

26.2 N-[1-Methylpyrrolo[2,3-b]pyrid-5-yl]-5-fluoro-1-[(3-fluorophenyl)methyl]-1H-indole-2-carboxamide (Compound 26)

0.4 g (1.4 mmol) of the amide prepared in the preceding step, 0.32 g (1.54 mmol) of 5-bromo-1-methylpyrrolo[2,3-b]pyridine (*Heterocycles* 2003, 60(4) 865), 0.08 g (0.42 mmol) of copper iodide, 0.39 g (2.79 mmol) of potassium carbonate and 10 mL of dry dioxane are placed in a pressure tube equipped with a magnetic stirrer. The suspension is degassed, 53 mg (0.46 mmol) of trans-cyclohexane-1,2-diamine are then added, and the tube is sealed and heated at 120° C. with stirring for 16 hours. After this time, 50 mL of ethyl acetate and 50 mL of water are added to the medium. The aqueous phase is separated out and then extracted with 2×30 mL of ethyl acetate. The organic phases are combined, washed with 50 mL of water, dried over sodium sulfate and then concentrated under reduced pressure. The resulting product is purified by chromatography on a column of silica, eluting with a mixture of dichloromethane and acetone, and then by recrystallization from isopropyl alcohol.

m.p.: 203-204° C.

$^1$H NMR (DMSO D$_6$), δ (ppm): 10.51 (s, 1H); 8.51 (s, 1H); 8.36 (s, 1H); 7.59 (m, 2H); 7.55 (s, 1H); 7.46 (s, 1H); 7.32 (m, 1H); 7.19 (m, 1H); 7.08 (m, 1H); 6.93 (m, 2H); 6.49 (s, 1H); 5.9 (s, 2H); 3.82 (s, 3H).

EXAMPLE 27

Compound 11

N-(1-Methyl-1H-pyrrolo[2,3-b]pyrid-5-yl)-5-trifluoromethyl-1-[(3-fluorophenyl)-methyl]-1H-indole-2-carboxamide This compound was prepared according to a method similar to that of Example 26.

m.p.: 249-250° C.

¹H NMR (DMSO D$_6$), δ (ppm): 8.5 (s, 1H); 8.36 (s, 1H); 8.22 (s, 1H); 7.81 (m, 1H); 7.6 (m, 2H); 7.54 (s, 1H); 7.32 (m, 1H); 7.07 (m, 1H); 6.97 (m, 2H); 6.49 (s, 1H); 5.99 (s, 2H); 3.82 (s, 3H).

EXAMPLE 28

Compound 13

N-(1-Methyl-1H-pyrrolo[2,3-b]pyrid-5-yl)-5-trifluoromethyl-1-[(3-fluorophenyl)-methyl]-1H-pyrrolo[2,3-b]pyridine-2-carboxamide This compound was prepared according to a method similar to that of Example 26.

m.p.: 237-238° C.

¹H NMR (DMSO D$_6$), δ (ppm): 10.69 (s, 1H); 8.82 (s, 1H); 8.76 (s, 1H); 8.49 (s, 1H); 8.33 (s, 1H); 7.62 (s, 1H); 7.53 (d, 1H); 7.32 (m, 1H); 7.07 (m, 1H); 6.99 (m, 2H); 6.5 (d, 1H); 6.00 (s, 2H); 3.82 (s, 3H).

EXAMPLE 29

Compound 14

N-[1-Methyl-2,3-dihydro-1H-pyrrolo[2,3-b]pyrid-5-yl]-5-fluoro-1-[(3-fluorophenyl)-methyl]-1H-indole-2-carboxamide 29.1
5-Bromo-2,3-dihydro-1-methylpyrrolo[2,3-b]pyridine To a suspension stirred at 0° C., under an inert atmosphere, of 0.48 g (12.06 mmol) of 60% sodium hydride in 5 mL of dimethylformamide is added dropwise a solution of 5-bromo-2,3-dihydro-1H-pyrrolo[2,3-b]pyridine in 10 mL of dimethylformamide. The mixture is stirred at 0° C. for 15 minutes and then at 20° C. for 45 minutes. A solution of 0.77 mL (12.06 mmol) of methyl iodide in 5 mL of dimethylformamide is then added to this stirred suspension at 0° C. The mixture is then stirred for 48 hours. After this time, 50 mL of water and 50 mL of ethyl acetate are added to the mixture. The aqueous phase is separated out and then extracted with 3×30 mL of ethyl acetate. The organic phases are combined, washed with 2×50 mL of water and then concentrated under reduced pressure. The resulting product is purified by chromatography on a column of silica, eluting with a mixture of dichloromethane and methanol. 0.97 g of the expected product is thus isolated.

LC-MS: 213 [M+H]$^+$

¹H NMR (DMSO D$_6$), δ (ppm): 7.81 (s, 1H); 7.39 (s, 1H); 3.46 (t, 2H); 2.94 (t, 2H); 2.82 (s, 3H).

29.2 N-[1-Methyl-2,3-dihydro-1H-pyrrolo[2,3-b]pyrid-5-yl]-5-fluoro-1-[(3-fluorophenyl)-methyl]-1H-indole-2-carboxamide (Compound 14)

This compound was prepared according to a method similar to that of Example 26.

m.p.: 189-191° C.

¹H NMR (DMSO D$_6$), δ (ppm): 10.21 (s, 1H); 8.06 (s, 1H); 7.65 (s, 1H); 7.57 (m, 2H); 7.35 (m, 2H); 7.18 (m, 1H); 7.05 (m, 1H); 6.91 (m, 2H); 5.9 (s, 2H); 3.42 (t, 2H); 2.95 (t, 2H); 2.85 (s, 3H).

EXAMPLE 30

Compound 15

N-(1-Methyl-1H-pyrrolo[2,3-b]pyrid-5-yl)-1-[[(3-trifluoromethyl)phenyl]methyl]-1H-indole-2-carboxamide This compound was prepared according to a method similar to that of Example 26.

m.p.: 211-212° C.

¹H NMR (DMSO D$_6$), δ (ppm): 10.49 (s, 1H); 8.51 (s, 1H); 8.35 (s, 1H); 7.79 (d, 1H); 7.54 (m, 6H); 7.39 (m, 1H); 7.31 (m, 1H); 7.19 (m, 1H); 6.47 (s, 1H); 6.0 (s, 2H); 3.84 (s, 3H).

EXAMPLE 31

Compound 28

N-(1-Methyl-1H-pyrrolo[2,3-b]pyrid-5-yl)-5-fluoro-1-[(pyrid-4-yl)methyl)]-1H-indole-2-carboxamide This compound was prepared according to a method similar to that of Example 26.

m.p.: 176-177° C.

¹H NMR (DMSO D$_6$), δ (ppm): 10.51 (s, 1H); 8.7-8.4 (broad peak+s, 3H); 8.35 (s, 1H); 7.59 (m, 2H); 7.5 (m, 2H); 7.2 (m, 2H); 7.09 (broad peak, 1H); 6.48 (s, 1H); 5.91 (s, 2H); 3.85 (s, 3H).

EXAMPLE 32

Compound 29

N-(1-Methyl-1H-pyrrolo[2,3-b]pyrid-5-yl)-5-fluoro-1-[(pyrid-3-yl)methyl)]-1H-indole-2-carboxamide This compound was prepared according to a method similar to that of Example 26.

m.p.: 214-215° C.

¹H NMR (DMSO D$_6$), δ (ppm): 10.52 (s, 1H); 8.51 (s, 1H); 8.46 (s, 2H); 8.37 (s, 1H); 7.69 (m, 1H); 7.55 (m, 4H); 7.34 (m, 1H); 7.19 (m, 1H); 6.49 (s, 1H); 5.95 (s, 2H); 3.82 (s, 3H).

EXAMPLE 33

Compound 16

N-[1-Methyl pyrrolo[2,3-b]pyrid-6-yl]-5-fluoro-1-[(3-fluorophenyl)methyl]-1H-indole-2-carboxamide 33.1 6-Bromo-1-methylpyrrolo[2,3-b]pyridine This compound was prepared according to a method similar to that of Example 29.1 starting with commercial 6-bromo-1H-pyrrolo[2,3-b]pyridine.

LC-MS: 211 [M+H]$^+$

¹H NMR (DMSO D$_6$), δ (ppm): 7.92 (d, 1H); 7.53 (s, 1H); 7.28 (d, 1H); 6.5 (s, 1H); 3.82 (s, 3H).

33.2 N-[1-Methylpyrrolo[2,3-b]pyrid-6-yl]-5-fluoro-1-[(3-fluorophenyl)methyl]-1H-indole-2-carboxamide (Compound 16)

This compound was prepared according to a method similar to that of Example 26 starting with 6-bromo-1-methylpyrrolo[2,3-b]pyridine prepared in the preceding step.

m.p.: 189-191° C.

¹H NMR (DMSO D₆), δ (ppm): 10.8 (s, 1H); 7.99 (d, 1H); 7.81 (d, 1H); 7.59 (m, 2H); 7.53 (m, 1H); 7.45 (s, 1H); 7.32 (m, 1H); 7.18 (m, 1H); 7.05 (m, 1H); 6.91 (m, 2H); 6.49 (s, 1H); 5.93 (s, 2H); 3.84 (s, 3H).

EXAMPLE 34

Compound 17

N-(1-Methyl-1H-pyrrolo[2,3-b]pyri d-5-yl)-5-fluoro-1-[[(3-trifluoromethyl)phenyl]-methyl]-1H-indole-2-carboxamide This compound was prepared according to a method similar to that of Example 26.
m.p.: 181-182° C.
¹H NMR (DMSO D₆), δ (ppm): 10.56 (s, 1H); 8.5 (s, 1H); 8.32 (s, 1H); 7.45-7.7 (m, 7H); 7.38 (m, 1H); 7.15 (m, 1H); 6.48 (s, 1H); 6.0 (s, 2H); 3.79 (s, 3H).

EXAMPLE 35

Compound 18

N-(1-Methyl-1H-pyrrolo[2,3-b]pyrid-5-yl)-5-fluoro-1-[(3-methyl phenyl)methyl]-1H-indole-2-carboxamide This compound was prepared according to a method similar to that of Example 26.
m.p.: 185-186° C.
¹H NMR (DMSO D₆), δ (ppm): 10.51 (s, 1H); 8.5 (s, 1H); 8.37 (s, 1H); 7.56 (m, 3H); 7.4 (s, 1H); 7.16 (m, 2H); 7.0 (m, 2H); 6.87 (m, 1H); 6.48 (s, 1H); 5.87 (s, 2H); 3.82 (s, 3H); 2.2 (s, 3H).

EXAMPLE 36

Compound 32

N-(1H-Pyrrolo[2,3-b]pyrid-5-yl)-5-trifluoromethyl-1-[(thiazol-2-yl)methyl]-1H-indole-2-carboxamide This compound was prepared according to a protocol similar to that described in Example 5.
m.p.: 218-219° C.
¹H NMR (DMSO D₆), δ (ppm): 11.9 (s, 1H); 10.75 (s, 1H); 8.6 (s, 1H); 8.5 (s, 1H); 8.2 (s, 1H); 7.95 (d, 1H); 7.7 (d, 1H); 7.65 (m, 3H); 7.5 (m, 1H); 6.55 (m, 1H); 6.2 (s, 2H).

EXAMPLE 37

Compound 33

N-(1H-Pyrrolo[2,3-b]pyrid-5-yl)-6-trifluoromethyl-1-[(thiazol-2-yl)methyl]-1H-indole-2-carboxamide This compound was prepared according to a protocol similar to that described in Example 5.
m.p.: 165-166° C.

¹H NMR (DMSO D₆), δ (ppm): 11.8 (s, 1H); 10.7 (s, 1H); 8.6 (s, 1H); 8.45 (s, 1H); 8.2 (s, 1H); 7.95 (d, 1H); 7.75 (d, 1H); 7.6 (m, 2H); 7.5 (m, 2H); 6.55 (m, 1H); 6.3 (s, 2H).

EXAMPLE 38

Compound 34

N-(1H-Pyrrolo[2,3-b]pyrid-5-yl)-5-trimethylsilyl-1-[(thiazol-2-yl)methyl]-1H-indole-2-carboxamide

38.1 Ethyl (5-trimethylsilyl-1-[(thiazol-2-yl)methyl]-1H-indole-2-carboxylate (Compound IIe)

This compound was prepared according to a process similar to that described in step 5.1 by reacting ethyl 5-trimethylsilyl-1H-indole-2-carboxylate prepared according to the process described in step 10.4 with (thienyl-2-yl)methanol in the presence of (cyanomethylene)tributylphosphorane (CMBP). The crude reaction product is then purified by flash chromatography on a column of silica gel to give the expected product.
¹H NMR (DMSO D₆), δ (ppm): 7.80 (s, 1H); 7.64 (d, 1H); 7.61 (d, 1H); 7.51 (d, 1H); 7.40 (d, 1 H); 7.30 (s, 1H); 6.04 (s, 2H) 4.24 (q, 2H); 1.23 (t, 3H); 0.19 (s, 9H).

38.2 N-(1H-Pyrrolo[2,3-b]pyrid-5-yl)-5-trimethylsilyl-1-[(thiazol-2-yl)methyl]-1H-indole-2-carboxamide (Compound 34)

This compound was prepared according to a protocol similar to that described in Example 5.
m.p.: 213-214° C.
¹H NMR (DMSO D₆), δ (ppm): 11.7 (s, 1H); 10.45 (s, 1H); 8.5 (d, 1H); 8.35 (d, 1H); 7.9 (s, 1H); 7.75-7.65 (m, 2H); 7.6 (d, 1H); 7.5-7.4 (m, 3H); 6.5 (m, 1H); 6.2 (s, 2H); 0.3 (s, 9H).

EXAMPLE 39

Compound 35

N-(1H-Pyrrolo[2,3-b]pyrid-5-yl)-6-fluoro-1-[(thiazol-2-yl)methyl]-1H-indole-2-carboxamide This compound was prepared according to a protocol similar to that described in Example 5.
m.p.: 255-256° C.
¹H NMR (DMSO D₆), δ (ppm): 11.6 (s, 1H); 10.45 (s, 1H); 8.45 (d, 1H); 8.35 (d, 1H); 7.75 (m, 2H); 7.65-7.45 (m, 4H); 7.05 (m, 1H); 6.45 (m, 1H); 6.2 (s, 2H).

EXAMPLE 40

Compound 38

N-(1H-Pyrrolo[2,3-b]pyrid-5-yl)-6-trimethylsilyl-1-[(pyrid-4-yl)methyl)]-1H-indole-2-carboxamide

40.1 Ethyl (6-trimethylsilyl-1-[(pyrid-2-yl)methyl]-1H-indole-2-carboxylate (Compound IIh)

This compound was prepared according to a process similar to that described in step 5.1 by reacting ethyl 6-trimethylsilyl-1H-indole-2-carboxylate prepared according to the process described in step 9.2 with (pyrid-2-yl)methanol in the presence of (cyanomethylene)tributylphosphorane (CMBP).

The crude reaction product is then purified by flash chromatography on a column of silica gel to give the expected product.

$^1$H NMR (DMSO D$_6$), δ (ppm): 8.2 (d, 2H); 7.49 (d, 1H); 7.42 (s, 1H); 7.15 (s, 1H); 7.05 (d, 1H); 6.70 (d, 2H); 5.68 (s, 2H); 4.01 (q, 2H); 1.01 (t, 3H); 0.0 (s, 9H).

40.2 N-(1H-Pyrrolo[2,3-b]pyrid-5-yl)-6-trimethylsilyl-1-[(pyrid-4-yl)methyl)]-1H-indole-2-carboxamide (Compound 38)

This compound was prepared according to a protocol similar to that described in Example 5.

m.p.: 235-236° C.

$^1$H NMR (DMSO D$_6$), δ (ppm): 8.45 (m, 3H); 8.30 (d, 1H); 7.75 (d, 1H); 7.65 (s, 1H); 7.5 (m, 2H); 7.3 (d, 1H); 7.0 (d, 2H); 6.45 (d, 1H); 6.0 (s, 2H); 0.25 (s, 9H).

EXAMPLE 41

Compound 39

N-(1H-Pyrrolo[2,3-b]pyrid-5-yl)-5-trimethylsilyl-1-[(pyrid-4-yl)methyl)]-1H-indole-2-carboxamide 41.1 Ethyl (5-trimethylsilyl-1-[(pyrid-4-yl)methyl]-1H-indole-2-carboxylate (Compound IIg)

This compound was prepared according to a process similar to that described in step 5.1 by reacting ethyl 5-trimethylsilyl-1H-indole-2-carboxylate prepared according to the process described in step 10.4 with (pyrid-2-yl)methanol in the presence of (cyanomethylene)tributylphosphorane (CMBP). The crude reaction product is then purified by flash chromatography on a column of silica gel to give the expected product.

$^1$H NMR (DMSO D$_6$), δ (ppm): 8.37 (d, 2H), 7.83 (s, 1H), 7.47 (d, 1H), 7.37 (d, 1H), 7.34 (s, 1H), 6.84 (d, 2H), 5.80 (s, 2H), 4.18 (q, 2H), 1.18 (t, 3H), 0.19 (s, 9H).

41.2 N-(1H-Pyrrolo[2,3-b]pyrid-5-yl)-5-trimethylsilyl-1-[(pyrid-4-yl)methyl)]-1H-indole-2-carboxamide (Compound 39)

This compound was prepared according to a protocol similar to that described in Example 5.

m.p.: 279-281° C.

$^1$H NMR (DMSO D$_6$), δ (ppm): 8.45 (m, 3H); 8.30 (d, 1H); 7.9 (s, 1H); 7.6-7.35 (m, 4H); 7.0 (d, 2H); 6.45 (m, 1H); 5.9 (s, 2H); 0.3 (s, 9H).

EXAMPLE 42

Compound 40

N-(1H-Pyrrolo[2,3-b]pyrid-5-yl)-6-fluoro-1-[(pyrid-4-yl)methyl)]-1H-indole-2-carboxamide This compound was prepared according to a protocol similar to that described in Example 5.

m.p.: 284-286° C.

$^1$H NMR (DMSO D$_6$), δ (ppm): 11.6 (s, 1H); 10.4 (s, 1H); 8.45 (d, 2H); 8.4 (d, 1H); 8.3 (s, 1H); 7.8 (m, 1H); 7.55 (s, 1H); 7.45 (m, 2H); 7.0 (m, 3H); 6.45 (m, 1H); 5.9 (s, 2H).

EXAMPLE 43

Compound 43

N-(1H-Pyrrolo[2,3-b]pyrid-5-yl)-5-trifluoromethyl-1-(3-fluorobenzyl)-1H-indole-2-carboxamide This compound was prepared according to a protocol similar to that described in Example 1.3.

m.p.: 286-287° C.

$^1$H NMR (DMSO D$_6$), δ (ppm): 11.61 (s, 1H); 10.62 (s, 1H); 8.47 (s, 1H); 8.35 (s, 1H); 8.21 (s, 1H); 7.82 (d, 1H); 7.6 (m, 2H); 7.5 (s, 1H); 7.33 (m, 1H); 7.08 (m, 1H); 6.98 (m, 2H); 6.48 (s, 1H); 5.98 (s, 2H).

EXAMPLE 44

Compound 44

N-(1-Methyl-1H-pyrrolo[2,3-b]pyrid-5-yl)-1-[(3-fluorophenyl)methyl]-1H-pyrrolo[2,3-c]pyridine-2-carboxamide This compound was prepared according to a protocol similar to that described in Example 26.

m.p.: 225-227° C.

$^1$H NMR (DMSO D$_6$), δ (ppm): 10.8 (s, 1H); 9.08 (s, 1H); 8.49 (d, 1H); 8.38 (d, 1H); 8.27 (d, 1H); 7.72 (d, 1H); 7.55 (d, 1H); 7.47 (s, 1H); 7.32 (m, 1H); 7.02 (m, 3H); 6.45 (m, 1H); 5.95 (s, 2H); 3.82 (s, 3H).

EXAMPLE 45

Compound 45

N-(1H-pyrrolo[2,3-b]pyrid-5-yl)-1-[(3-fluorophenyl)methyl]-1H-pyrrolo[2,3-c]pyridine-2-carboxamide This compound was prepared according to a protocol similar to that described in Example 26.

m.p.: 270-271° C.

$^1$H NMR (DMSO D$_6$), δ (ppm): 11.62 (s, 1H); 10.68 (s, 1H); 9.04 (s, 1H); 8.49 (d, 1H); 8.38 (d, 1H); 8.28 (d, 1H); 7.73 (d, 1H); 7.4 (m, 3H); 7.05 (m, 3H); 6.49 (s, 1H); 6.01 (s, 2H).

EXAMPLE 46

Compound 46

N-(1H-Pyrrolo[2,3-b]pyrid-5-yl)-5-fluoro-1-[(pyrid-4-yl)methyl)]-1H-indole-2-carboxamide This compound was prepared according to a protocol similar to that described in Example 5.

m.p.: 259-260° C.

¹H NMR (DMSO D₆), δ (ppm): 11.6 (s, 1H); 10.5 (s, 1H); 8.48 (m, 3H); 8.3 (s, 1H); 7.55 (m, 2H); 7.48 (m, 2H); 7.18 (m, 1H); 7.02 (m, 2H); 6.45 (s, 1H); 5.95 (s, 2H).

EXAMPLE 47

Compound 47

N-(1-Methyl-1H-Pyrrolo[2,3-b]pyrid-5-yl)-5-trifluoromethyl-1-[(pyrid-4-yl)methyl)]-1H-indole-2-carboxamide This compound was prepared according to a protocol similar to that described in Example 5.

m.p.: 213-214° C.

¹H NMR (DMSO D₆), δ (ppm): 10.63 (s, 1H); 8.49 (m, 3H); 8.35 (s, 1H); 8.27 (s, 1H); 7.78 (d, 1H); 7.7 (s, 1H); 7.6 (d, 1H); 7.52 (d, 1H); 7.04 (m, 2H); 6.49 (s, 1H); 6.02 (s, 2H); 3.82 (s, 3H).

Table I that follows illustrates the chemical structures and the physical properties of a number of examples of compounds according to the invention.

In this table:
- the column "m.p. (° C.)" indicates the melting points of the products in degrees Celsius (° C.);
- all the compounds are in the form of the free base,
- W represents an oxygen atom;
- Z₂ represents a carbon atom bonded to the nitrogen atom of the amide of formula (I);
- n is equal to 1;
- R represents a substituent on the phenyl group;
- "Me" corresponds to a methyl group.

TABLE 1

| No. | X1, X2, X3, X4 | R | (Ra/Rb aryl) | m.p. (°C.) |
|---|---|---|---|---|
| 1 | CH, C—F, CH, CH | F | 5-methyl-1-acetyl-2,3-dihydro-1H-pyrrolo[2,3-b]pyridine | 186-188 |
| 2 | CH, C—F, CH, CH | F | 5-methyl-1H-pyrrolo[2,3-b]pyridine | 266-267 |
| 3 | CH, C—F, CH, CH | F | 5-methyl-2,3-dihydro-1H-pyrrolo[2,3-b]pyridine | 230-232 |
| 4 | CH, C—F, CH, CH | F | 5-methyl-1H-pyrrolo[3,2-b]pyridine | 277-278 |
| 5 | CH, CH, C—F, CH | Me | 5-methyl-1H-pyrrolo[2,3-b]pyridine | 310-311 |
| 6 | CH, CH, C—Si(Me)₃, CH | CF₃ | 5-methyl-1H-pyrrolo[2,3-b]pyridine | 251-252 |
| 7 | CH, C—Si(Me)₃, CH, CH | CF₃ | 5-methyl-1H-pyrrolo[2,3-b]pyridine | 199-200 |
| 8 | CH, C—F, CH, CH | F | 5-methyl-1H-pyrrolo[3,2-c]pyridine | 203-204 |
| 9 | CH, C—CF₃, CH, N | F | 5-methyl-1H-pyrrolo[2,3-b]pyridine | 319-320 |
| 10 | CH, C—F, CH, CH | F | 5-methyl-1H-pyrrolo[2,3-b]pyridine 7-oxide | 260-263 |

TABLE 1-continued (I)

| No. | X1, X2, X3, X4 | R | Ra/Rb group (Z1,Z2,Z3,Z4 with Ra, Rb) | m.p. (°C.) |
|---|---|---|---|---|
| 11 | CH, C—CF₃, CH, CH | F | 5-methyl-1-methyl-7-azaindole | 249-250 |
| 12 | CH, C—F, CH, CH | F | 5-methyl-1-methyl-7-azaindole | 203-204° C. |
| 13 | CH, C—CF₃, CH, N | F | 5-methyl-1-methyl-7-azaindole | 237-238 |
| 14 | CH, C—F, CH, CH | F | 5-methyl-1-methyl-2,3-dihydro-7-azaindole | 189-191 |
| 15 | CH, CH, CH, CH | CF₃ | 5-methyl-1-methyl-7-azaindole | 211-212 |
| 16 | CH, C—F, CH, CH | F | 6-methyl-1-methyl-7-azaindole | 189-191 |
| 17 | CH, C—F, CH, CH | CF₃ | 5-methyl-1-methyl-7-azaindole | 181-182 |
| 18 | CH, C—F, CH, CH | Me | 5-methyl-1-methyl-7-azaindole | 185-186 |
| 19 | CH, C—CF₃, CH, CH | Me | 5-methyl-7-azaindole (NH) | 311-312 |
| 20 | CH, CH, C—CF₃, CH | Me | 5-methyl-7-azaindole (NH) | 278-279 |
| 21 | CH, C—Si(Me)₃, CH, CH | Me | 6-methyl-7-azaindole (NH) | 327-328 |
| 22 | CH, C—CF₃, CH, CH | Me | 5-methyl-7-azaindole (NH) | 305-306 |
| 23 | CH, CH, C—Si(Me)₃, CH | Me | 5-methyl-7-azaindole (NH) | 202-203 |
| 24 | CH, C—CF₃, CH, CH | CF₃ | 5-methyl-7-azaindole (NH) | 247-248 |
| 25 | CH, CH, C—CF₃, CH | CF₃ | 5-methyl-7-azaindole (NH) | 334-335 |
| 26 | CH, C—CF₃, CH, N | CF₃ | 6-methyl-7-azaindole (NH) | 273-274 |

TABLE 1-continued

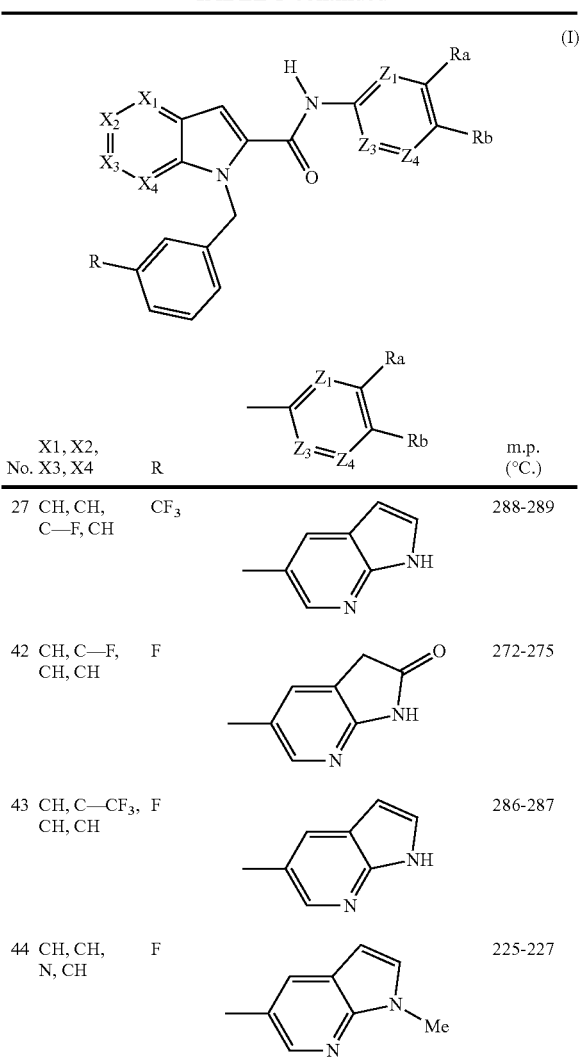

| No. | X1, X2, X3, X4 | R | [aryl] | m.p. (°C.) |
|---|---|---|---|---|
| 27 | CH, CH, C—F, CH | CF$_3$ | 5-methyl-7-azaindole | 288-289 |
| 42 | CH, C—F, CH, CH | F | 5-methyl-2-oxo-2,3-dihydro-7-azaindole | 272-275 |
| 43 | CH, C—CF$_3$, CH, CH | F | 5-methyl-7-azaindole | 286-287 |
| 44 | CH, CH, N, CH | F | 1,5-dimethyl-7-azaindole | 225-227 |

TABLE 1-continued

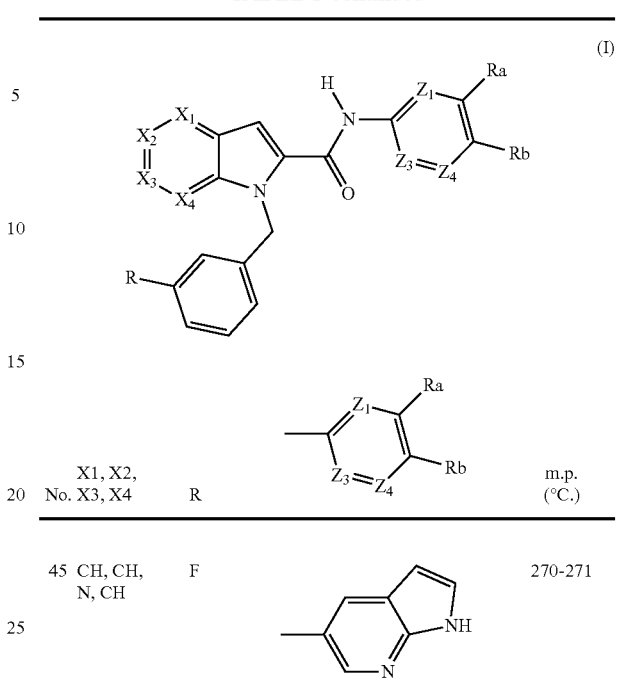

| No. | X1, X2, X3, X4 | R | [aryl] | m.p. (°C.) |
|---|---|---|---|---|
| 45 | CH, CH, N, CH | F | 5-methyl-7-azaindole | 270-271 |

Table 2 that follows illustrates the chemical structures and the physical properties of a number of compounds according to the invention.

In this table:

the column "m.p. (° C.)" indicates the melting points of the products in degrees Celsius (° C.);

all the compounds are in the form of the free base,

W represents an oxygen atom;

Z$_2$ represents a carbon atom bonded to the nitrogen atom of the amide of formula (I);

n is equal to 1.

TABLE 2

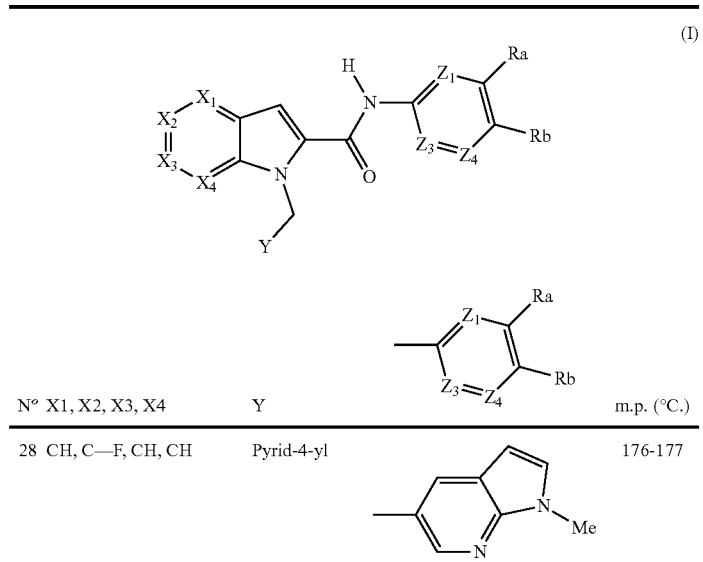

| N° | X1, X2, X3, X4 | Y | [aryl] | m.p. (°C.) |
|---|---|---|---|---|
| 28 | CH, C—F, CH, CH | Pyrid-4-yl | 1,5-dimethyl-7-azaindole | 176-177 |

TABLE 2-continued (I)

| N° | X1, X2, X3, X4 | Y | [Ring] | m.p. (°C.) |
|---|---|---|---|---|
| 29 | CH, C—F, CH, CH | Pyrid-3-yl | 5-methyl-1-methyl-7-azaindole | 214-215 |
| 30 | CH, C—CF₃, CH, N | Thiazol-2-yl | 5-methyl-7-azaindole | 274-275 |
| 31 | CH, CH, C—Si(Me)₃, CH | Thiazol-2-yl | 5-methyl-7-azaindole | 269-270 |
| 32 | CH, C—CF₃, CH, CH | Thiazol-2-yl | 5-methyl-7-azaindole | 218-219 |
| 33 | CH, C—CF₃, CH, CH | Thiazol-2-yl | 5-methyl-7-azaindole | 165-166 |
| 34 | CH, C—Si(Me)₃, CH, CH | Thiazol-2-yl | 5-methyl-7-azaindole | 213-214 |
| 35 | CH, CH, C—F, CH | Thiazol-2-yl | 5-methyl-7-azaindole | 255-256 |
| 36 | CH, C—CF₃, CH, CH | Pyrid-4-yl | 5-methyl-7-azaindole | 216-217 |
| 37 | CH, CH, C—CF₃, CH | Pyrid-4-yl | 5-methyl-7-azaindole | 311-313 |

TABLE 2-continued

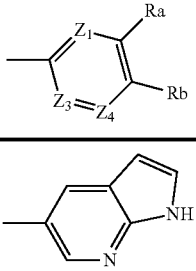

(I)

| N° | X1, X2, X3, X4 | Y | Ra/Rb group | m.p. (°C.) |
|---|---|---|---|---|
| 38 | CH, CH, C—Si(Me)₃, CH | Pyrid-4-yl | 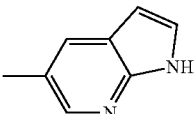 | 235-236 |
| 39 | CH, C—Si(Me)₃, CH, CH | Pyrid-4-yl | 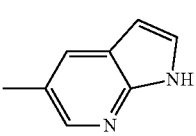 | 279-281 |
| 40 | CH, CH, C—F, CH | Pyrid-4-yl | 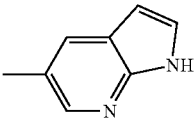 | 284-286 |
| 41 | CH, C—CF₃, CH, N | Pyrid-4-yl | 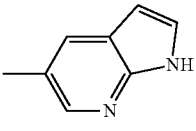 | 296-298 |
| 46 | CH, C—F, CH, CH | Pyrid-4-yl | 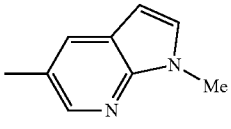 | 259-260 |
| 47 | CH, C—CF₃, CH, CH | Pyrid-4-yl | (N-Me 7-azaindole) | 213-214 |

The compounds according to the invention underwent in vitro and in vivo pharmacological tests that demonstrated their value as therapeutically active substances. These compounds have antagonist or agonist activity towards the TRPV1 (or VR1) receptors.

Test of inhibition of the current induced with capsaicin on rat DRGs

Primary culture of rat dorsal root ganglion (DRG) cells:
DRG neurones naturally express the TRPV1 receptor.

The primary cultures of newborn rat DRGs are prepared using 1-day-old rats. Briefly, after dissection, the ganglions are trypsinized and the cells dissociated by mechanical trituration. The cells are resuspended in an Eagle basal culture medium containing 10% foetal calf serum, 25 mM KCl, 2 mM glutamine, 100 μg/ml gentamicin and 50 ng/ml of NGF, and then deposited on glass slides coated with laminin (0.25× 10⁶ cells per slide), which are then placed in Corning 12-well dishes. The cells are incubated at 37° C. in a humidified atmosphere containing 5% CO₂ and 95% air. Cytosine β-D-arabinoside (1 μM) is added 48 hours after culturing, to prevent the growth of non-neuronal cells. The slides are transferred into experimental chambers for the patch-clamp studies after 7-10 days of culturing.

Electrophysiology:

The measuring chambers (volume 800 μl) containing the cell preparation are placed on the platform of an inverted microscope (Olympus IMT2) equipped with Hoffman optics (Modulation Contrast, New York) and observed at a magnification of 400×. The chambers are continuously gravity-influxed (2.5 ml/min) using a solution distributor accepting 8 inlets and whose sole outlet, consisting of a polyethylene tube (aperture 500 μm), is placed less than 3 mm from the cell under study. The "whole cell" configuration of the patch-clamp technique was used. The borosilicate-glass pipettes (resistance 5-10 MOhms) are brought to the cell by means of a 3D piezoelectric micromanipulator (Burleigh, PC1000). The overall currents (membrane potential set at −60 mV) are recorded with an Axopatch 1D amplifier (Axon Instruments, Foster City, Calif.), connected to a PC running the Pclamp8 software (Axon Instrument). The current plots are recorded on paper and simultaneously digitized (sampling frequency 15 to 25 Hz) and acquired on the hard drive of the PC.

The application of a 300 nM capsaicin solution induces on the DRG cells (voltage set at −70 mV) an entering cationic current. In order to minimize the desensitization of the receptors, a minimum interval of 1 minute between two applications of capsaicin is observed. After a control period (stabilization of the capsaicin response alone), the test compounds are applied alone at a given concentration (concentration of 10 nM or 1 nM) for a time of 4 to 5 minutes, during which several capsaicin+compound tests are performed (to obtain the maximum inhibition). The results are expressed as a percentage of inhibition of the control capsaicin response.

In the case of the VR1 antagonist compounds, the percentages of inhibition of the capsaicin response (1 µM) are between 20% and 100% for the most active compounds of the invention tested at concentrations of from 0.1 to 100 nM. They are therefore effective antagonists of receptors of TRPV1 type. Table 3 gives an example of the percentage of inhibition obtained with the compounds of the invention.

TABLE 3

| Compound No. | % inhibition in DRG patch |
|---|---|
| 2 | 82% (1 nM) |
| 8 | 67.5% (100 nM) |

Pain induced by intraplantar administration of capsaicin to mice.

The intraplantar injection of capsaicin to mice rapidly produces short-lived nociceptive behaviour, which is reflected by licking, biting and flexing of the administered leg. These nociceptive responses are probably associated with the activation of the local TRPV1 receptors by the capsaicin.

Methodology:

(E)-Capsaicin is initially diluted to 3 mg/ml in DMSO, and then diluted again for its final use to 1.5 µg/20 µl in physiological saline. The administration of solvent has no effect on the behaviour of the mouse. The capsaicin is injected into the hind legs of the animal, on the upper face.

The test compounds are administered orally 120 minutes before the injection of capsaicin. Two hours after administration of the compounds, the mice are placed in a glass beaker. The nociceptive behaviour of the animals is then assessed immediately by the experimenter, and the duration of the capsaicin-induced behavioural manifestations is timed over a period of 2 minutes (licking and biting, total or partial flexure of the injected leg).

For each compound, an inhibition corresponding to the mean of the capsaicin-induced nociceptive responses, in response to a dose of test product (expressed in mg/kg) administered orally to a sample of a given number (n) of mice, is determined.

Table 4 gives an example of a percentage of inhibition obtained with the compounds of the invention.

TABLE 4

| Compound No. | Dose | n | % inhibition of the capsaicin-induced nociceptive responses |
|---|---|---|---|
| 2 | 10 mg/kg | 10 | 61% (±6%) |

The compounds of the invention may thus be used for the preparation of medicaments, especially for the preparation of a medicament for preventing or treating pathologies in which receptors of TRPV1 type are involved.

The compounds of the invention may be useful for preventing or treating pathologies in which receptors of TRPV1 type are involved.

Thus, a subject of the invention is medicaments comprising at least one compound of formula (I), or a pharmaceutically acceptable salt, or alternatively a hydrate or a solvate of the said compound.

These medicaments find their therapeutic use especially in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, animal bites or insect bites, post-herpetic neuralgia, muscular pain, trapped nerves (central and/or peripheral), spinal column and/or brain trauma, ischaemia (of the spinal column and/or the brain), neurodegeneration, haemorrhagic strokes (of the spinal column and/or of the brain) and post-stroke pain.

The compounds of the invention may also be used for preventing and/or treating metabolic disorders such as diabetes.

The compounds of the invention may be used for preventing and/or treating urological disorders such as hyperactivity of the bladder, vesical hyperreflexia, vesical instability, incontinence, urgent micturition, urinary incontinence, cystitis, nephritic colic, pelvic hypersensitivity and pelvic pain.

The compounds of the invention may be useful for preventing and/or treating gynaecological disorders, for instance vulvodynia and pain associated with salpingitis or with dysmenorrhoea.

These products may also be used for preventing and/or treating gastrointestinal disorders such as gastro-oesophageal reflux disorder, stomach ulcers, duodenal ulcers, functional dyspepsia, colitis, IBS, Crohn's disease, pancreatitis, oesophagitis and biliary colic.

Similarly, the products of the present invention may be useful in the prevention and/or treatment of respiratory disorders such as asthma, coughing, chronic obstructive pulmonary disease (COPD), bronchoconstriction and inflammatory disorders of the respiratory system.

These products may also be used for preventing and/or treating psoriasis, pruritus, dermal, ocular or mucous irritation, herpes and zona.

The compounds of the invention may also be used for treating depression.

The compounds of the invention may also be used for treating central nervous system diseases such as multiple sclerosis.

The compounds of the invention may also be used for treating cancers.

According to another of its aspects, the present invention relates to pharmaceutical compositions comprising, as active principle, at least one compound according to the invention.

These pharmaceutical compositions contain an effective dose of at least one compound according to the invention or a pharmaceutically acceptable salt, a hydrate or a solvate of the said compound and also at least one pharmaceutically acceptable excipient.

The said excipients are chosen, according to the pharmaceutical form and the desired mode of administration, from the usual excipients known to those skilled in the art.

The pharmaceutical compositions of the present invention may be administered via the oral, sublingual, subcutaneous, intramuscular, intravenous, topical, local, intratracheal, intranasal, transdermal or rectal route. These compositions may be administered in a unit administration form, as a mixture with standard pharmaceutical excipients. They are intended to be administered to animals and human beings for the prophylaxis or treatment of the disorders or diseases mentioned above.

The appropriate unit forms of administration include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.001 to 30 mg of active principle per kg of body weight, according to the galenical form.

There may be particular cases in which higher or lower dosages are appropriate: such dosages do not depart from the scope of the invention. According to the usual practice, the dosage that is appropriate for each patient is determined by the doctor according to the mode of administration, the weight and the response of the said patient.

The compounds of the invention may also be used for the preparation of medicaments, especially for the preparation of a medicament for preventing or treating pathologies in which receptors of TRPV1 type are involved, as mentioned previously.

According to another of its aspects, the present invention also relates to a method for treating the pathologies indicated above, which comprises the administration to a patient of an effective dose of a compound according to the invention, or a pharmaceutically acceptable salt, or hydrate or solvate thereof.

What is claimed is:

1. A compound of formula (I):

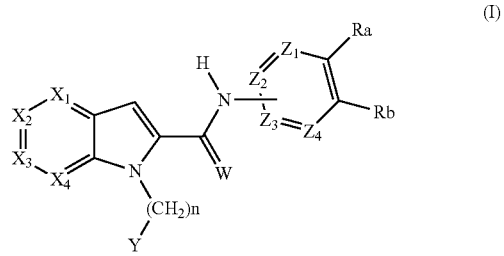

wherein:
$X_1$, $X_2$, $X_3$ and $X_4$ represent, independently of each other, a nitrogen atom or a group C—$R_1$;
wherein when one from among $X_1$, $X_2$, $X_3$ and $X_4$ represents a nitrogen atom, the others correspond to a group C—$R_1$;
$Z_1$, $Z_2$, $Z_3$ and $Z_4$ represent, independently of each other, a nitrogen atom, a carbon atom or a group C—$R_2$,
wherein at least one from among $Z_1$, $Z_2$, $Z_3$ and $Z_4$ corresponds to a nitrogen atom and one from among $Z_1$, $Z_2$, $Z_3$ and $Z_4$, corresponding to a carbon atom, being bonded to the nitrogen atom of the amide or of the thioamide of formula (I);
Ra and Rb form, together with the carbon atoms that bear them, a 5-membered ring, this ring comprising a nitrogen atom and carbon atoms, this ring being partially saturated or unsaturated and being optionally substituted with one or more substituents $R_3$;
W represents an oxygen or sulfur atom;
n is equal to 0, 1, 2 or 3;
Y represents an aryl or a heteroaryl optionally substituted with one or more groups chosen from a halogen atom, a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkyloxy, $C_3$-$C_7$-cycloalkyl-$C_1$-$C_6$-alkylene-O—, $C_1$-$C_6$-fluoroalkoxy, cyano, C(O)$NR_4R_5$, nitro, $NR_4R_5$, $C_1$-$C_6$-thioalkyl, thiol, —S(O)—$C_1$-$C_6$-alkyl, —S(O)$_2$—$C_1$-$C_6$-alkyl, $SO_2NR_4R_5$, $NR_6C(O)R_7$, $NR_6SO_2R_8$, C(O)$NR_4R_5$, OC(O)$NR_4R_5$, —Si—($C_1$-$C_6$-alkyl)$_3$, —$SF_5$, aryl-$C_1$-$C_5$-alkylene or aryl, heteroaryl-$C_1$-$C_5$-alkylene or heteroaryl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_6$-alkylene-O— being optionally substituted with a hydroxyl group, $C_1$-$C_6$-alkoxy and $NR_4R_5$, the aryl and heteroaryl groups being optionally substituted with one or more substituents $R_9$, which may be identical to or different from each other;
$R_1$ is chosen from a hydrogen atom, a halogen atom, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl -$C_1$-$C_3$-alkylenoxy-$C_1$-$C_6$-alkyl, arylthio-$C_1$-$C_6$-alkyl, heteroarylthio-$C_1$-$C_6$-alkyl, aryl-$C_1$-$C_3$-alkylene-thio-$C_1$-$C_6$-alkyl, heteroaryl-$C_1$-$C_3$-alkylene-thio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)$NR_4R_5$, nitro, $NR_4R_5$, $C_1$-$C_6$-thioalkyl, $C_3$-$C_7$-cycloalkylthio, $C_3$-$C_7$-cycloalkyl-$C_1$-$C_3$-alkylene-thio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, SO$_2$NR$_4$R$_5$, —Si—($C_1$-$C_6$-alkyl)$_3$, —SF$_5$, NR$_6$C(O)R$_7$, NR$_6$SO$_2$R$_8$, C(O)NR$_4$R$_5$, OC(O)NR$_4$R$_5$, aryl, heteroaryl, aryl-$C_1$-$C_5$-alkylene, heteroaryl-$C_1$-$C_5$-alkylene, aryloxy, arylthio, heteroaryloxy and heteroarylthio; the heteroaryl or aryl groups being optionally substituted with one or more substituents R$_9$, which may be identical to or different from each other;

R$_2$ represents a hydrogen atom, a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylene-O—, hydroxyl, thiol or $C_1$-$C_6$-fluoroalkoxy;

R$_3$ represents, when it is borne by a carbon atom, a hydrogen atom, a hydroxyl group, thiol, $C_1$-$C_6$-alkyl, $C_3$-$C_7$-cycloalkyl, $C_3$-$C_7$-cycloalkyl -$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl -$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene, C(O)NR$_4$R$_5$, C(O)O—$C_1$-$C_6$-alkyl, CO$_2$H, or an oxo or thio group; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene optionally being substituted with a hydroxyl group, $C_1$-$C_6$-alkoxy or NR$_4$R$_5$;

or

R$_3$ represents, when it is borne by a nitrogen atom, a hydrogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, aryl-S(O), $C_1$-$C_6$-alkyl-S(O)—, $C_1$-$C_6$-fluoroalkyl-S(O)—, aryl-S(O)$_2$—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $C_1$-$C_6$-alkyl-O—C(O)—, aryl-$C_1$-$C_3$-alkyl-O—C(O)—, $C_3$-$C_7$-cycloalkyl-O—C(O)—, $C_3$-$C_7$-cycloalkyl-$C_1$-$C_3$-alkylene-O—C(O)—, $C_1$-$C_6$-fluoroalkyl-O—C(O)—, aryl-O—C(O)—, heteroaryl-O—C(O)—, heteroaryl or aryl; the heteroaryl and aryl groups being optionally substituted with one or more substituents R$_9$; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, optionally being substituted with a hydroxyl group, $C_1$-$C_6$-alkoxy or NR$_4$R$_5$;

R$_4$ and R$_5$ represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl, or R$_4$ and R$_5$ together form, with the nitrogen atom that bears them, an azetidine, pyrrolidine, piperidine, azepine, morpholine, thiomorpholine, piperazine or homopiperazine group; the group NR$_4$R$_5$ being optionally substituted with a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$, $C_3$-$C_7$-cycloalkyl-S(O)$_2$—, $C_3$-$C_7$-cycloalkyl-$C_1$-$C_3$-alkylene-S(O)$_2$—, aryl -C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxyl, $C_1$-$C_6$-alkyloxy, $C_3$-$C_7$-cycloalkyloxy, $C_3$-$C_7$-cycloalkyl-$C_1$-$C_3$-alkylenoxy, $C_1$-$C_6$-fluoroalkyl, aryloxy-$C_1$-$C_6$-alkylene, aryloxy, heteroaryloxy-$C_1$-$C_6$-alkylene or heteroaryloxy;

R$_6$ and R$_7$ represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro and cyano;

or R$_6$ and R$_7$ together form a 4- to 7-membered lactam comprising the nitrogen atom and the C(O) group that bear them;

R$_8$ represents a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom, a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or R$_6$ and R$_8$ together form a 4- to 7-membered sultam comprising the nitrogen atom and the S(O)$_2$ group that bear them; and R$_9$ represents a halogen atom, a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, or $C_1$-$C_6$-fluoroalkoxy; these groups being optionally substituted with a group OH, $C_1$-$C_6$-alkoxy or NR$_4$R$_5$; or alternatively R$_9$ represents a nitro group, cyano or NR$_4$R$_5$;

the sulfur atom(s) of the compound of formula (I) optionally being in oxidized form;

the nitrogen atom(s) of the compound of formula (I) optionally being in oxidized form;

or an acid-addition salt thereof.

2. The compound of formula (I) according to claim 1, wherein:

X$_1$, X$_2$, X$_3$ and X$_4$ represent, independently of each other, a group C—R$_1$; R$_1$ is as defined in formula (I) according to claim 1;

or an acid-addition salt thereof.

3. The compound of formula (I) according to claim 1, wherein:

among X$_1$, X$_2$, X$_3$ and X$_4$, one from among X$_3$ and X$_4$ represents a nitrogen atom, and the others represent, independently of each other, a group C—R$_1$; R$_1$ being as defined in formula (I) according to claim 1;

or an acid-addition salt thereof.

4. The compound of formula (I) according to claim 1, wherein:

R$_1$ is chosen from a hydrogen atom, a halogen atom, a group $C_1$-$C_6$-fluoroalkyl and —Si($C_1$-$C_6$-alkyl)$_3$, or an acid-addition salt thereof.

5. The compound of formula (I) according to claim 1, wherein n is equal to 1;

or an acid-addition salt thereof.

6. The compound of formula (I) according to claim 1, wherein:

Y represents a phenyl, optionally substituted with one or more groups chosen from a halogen atom and a group $C_1$-$C_6$-alkyl or $C_1$-$C_6$-fluoroalkyl; or alternatively Y represents a pyridyl or a thiazolyl;

or an acid-addition salt thereof.

7. The compound of formula (I) according to claim 1, wherein:

W represents an oxygen atom;

or an acid-addition salt thereof.

8. The compound of formula (I) according to claim 1, wherein:

the group:

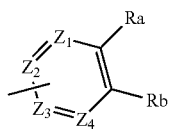

is chosen from the groups:

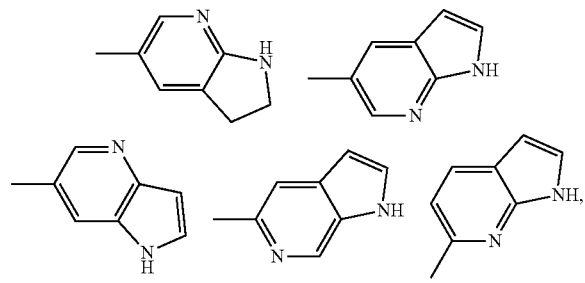

one from among $Z_1$, $Z_2$, $Z_3$ and $Z_4$ corresponding to a nitrogen atom and optionally being in oxidized form;

these groups being optionally substituted with $R_2$ and $R_3$ as defined in formula (I) according to claim 1;

$R_2$ represents a hydrogen atom;

$R_3$ represents, when it is borne by a carbon atom, a hydrogen atom or an oxo group;

$R_3$ represents, when it is borne by a nitrogen atom, a hydrogen atom or a group $C_1$-$C_6$-alkyl or $C_1$-$C_6$-alkyl-C(O)—;

or an acid-addition salt thereof.

9. The compound of formula (I) according to claim 1, wherein:

the group:

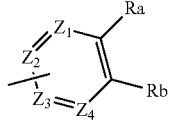

is chosen from the groups:

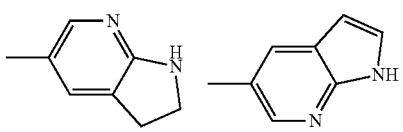

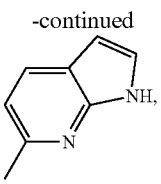

one from among $Z_1$, $Z_2$, $Z_3$ and $Z_4$ corresponding to a nitrogen atom and optionally being in oxidized form;

these groups being optionally substituted with $R_2$ and $R_3$ as defined in the formula (I);

$R_2$ represents a hydrogen atom;

$R_3$ represents, when it is borne by a carbon atom, a hydrogen atom or an oxo group;

$R_3$ represents, when it is borne by a nitrogen atom, a hydrogen atom or a group $C_1$-$C_6$-alkyl or $C_1$-$C_6$-alkyl-C(O)—;

or an acid-addition salt thereof.

10. The compound of formula (I) according to claim 1, wherein:

either $X_1$, $X_2$, $X_3$ and $X_4$ represent, independently of each other, a group C—$R_1$; or, among $X_1$, $X_2$, $X_3$ and $X_4$, one from among $X_3$ and $X_4$ represents a nitrogen atom, and the others represent, independently of each other, a group C—$R_1$;

$R_1$ is chosen from a hydrogen atom, a halogen atom and a group $C_1$-$C_6$-fluoroalkyl or —Si($C_1$-$C_6$-alkyl)$_3$;

n is equal to 1;

Y represents a phenyl, optionally substituted with one or more groups chosen from a halogen atom, a group $C_1$-$C_6$-alkyl or $C_1$-$C_6$-fluoroalkyl; or alternatively Y represents a pyridyl or a thiazolyl;

W represents an oxygen atom;

the group:

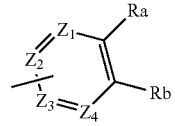

is chosen from the groups:

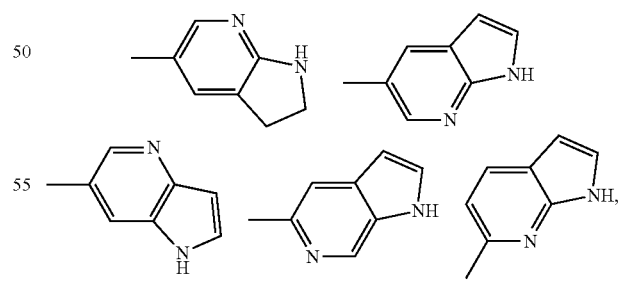

one from among $Z_1$, $Z_2$, $Z_3$ and $Z_4$ corresponding to a nitrogen atom and optionally being in oxidized form;

these groups being optionally substituted with $R_2$ and $R_3$ as defined in formula (I) according to claim 1;

$R_2$ represents a hydrogen atom;

$R_3$ represents, when it is borne by a carbon atom, a hydrogen atom or an oxo group;

R₃ represents, when it is borne by a nitrogen atom, a hydrogen atom or a group $C_1$-$C_6$-alkyl or $C_1$-$C_6$-alkyl-C(O)—;
or an acid-addition salt thereof.

11. A compound selected from the group consisting of:
N-(1-acetyl-2,3-dihydro-1H-pyrrolo[2,3-b]pyrid-5-yl)-5-fluoro-1-(3-fluorobenzyl)-1H-indole-2-carboxamide;
N-(1H-pyrrolo[2,3-b]pyrid-5-yl)-5-fluoro-1-(3-fluorobenzyl)-1H-indole-2-carboxamide;
N-(2,3-dihydro-1H-pyrrolo[2,3-b]pyrid-5-yl)-5-fluoro-1-(3-fluorobenzyl)-1H-indole-2-carboxamide;
N-(1H-pyrrolo[3,2-b]pyrid-6-yl)-5-fluoro-1-(3-fluorobenzyl)-1H-indole-2-carboxamide;
N-(1H-Pyrrolo[2,3-b]pyrid-5-yl)-6-fluoro-1-[(3-methylphenyl)methyl]-1H-indole-2-carboxamide;
N-(1H-Pyrrolo[2,3-b]pyrid-5-yl)-6-trimethylsilyl-1-[[(3-trifluoromethyl)phenyl]methyl]-1H-indole-2-carboxamide;
N-(1H-Pyrrolo[2,3-b]pyrid-5-yl)-5-trimethylsilyl-1-[[(3-trifluoromethyl)phenyl]methyl]-1H-indole-2-carboxamide;
N-(1H-Pyrrolo[2,3-c]pyrid-5-yl)-5-fluoro-1-[(3-fluorophenyl]methyl]-1H-indole-2-carboxamide;
N-(1H-Pyrrolo[2,3-b]pyrid-5-yl)-5-trifluoromethyl-1-[(3-fluorophenyl)methyl]-1H-pyrrolo[2,3-b]pyridine-2-carboxamide;
N-(7-Oxy-1H-pyrrolo[2,3-b]pyrid-5-yl)-5-fluoro-1-[(3-fluorophenyl)methyl]-1H-indole-2-carboxamide;
N-(1-Methyl-1H-pyrrolo[2,3-b]pyrid-5-yl)-5-trifluoromethyl-1-[(3-fluorophenyl)methyl]-1H-indole-2-carboxamide;
N-(1-Methyl-1H-pyrrolo[2,3-b]pyrid-5-yl)-5-fluoro-1-[(3-fluorophenyl)methyl]-1H-indole-2-carboxamide;
N-(1-Methyl-1H-pyrrolo[2,3-b]pyrid-5-yl)-5-trifluoromethyl-1-[(3-fluorophenyl)methyl]-1H-pyrrolo[2,3-b]pyridine-2-carboxamide;
N-(1-Methyl-2,3-dihydro-1H-pyrrolo[2,3-b]pyrid-5-yl)-5-fluoro-1-[(3-fluorophenyl)methyl]-1H-indole-2-carboxamide;
N-(1-Methyl-1H-pyrrolo[2,3-b]pyrid-5-yl)-1-[[(3-trifluoromethyl)phenyl]methyl]-1H-indole-2-carboxamide;
N-(1-Methyl-1H-pyrrolo[2,3-b]pyrid-6-yl)-5-fluoro-1-[(3-fluorophenyl)methyl]-1H-indole-2-carboxamide;
N-(1-Methyl-1H-pyrrolo[2,3-b]pyrid-5-yl)-5-fluoro-1-[[(3-trifluoromethyl)phenyl]-methyl]-1H-indole-2-carboxamide;
N-(1-Methyl-1H-pyrrolo[2,3-b]pyrid-5-yl)-5-fluoro-1-[(3-methylphenyl)methyl]-1H-indole-2-carboxamide;
N-(1H-pyrrolo[2,3-b]pyrid-5-yl)-5-trifluoromethyl-1-[(3-methylphenyl)methyl]-1H-indole-2-carboxamide;
N-(1H-pyrrolo[2,3-b]pyrid-5-yl)-6-trifluoromethyl-1-[(3-methylphenyl)methyl]-1H-indole-2-carboxamide;
N-(1H-pyrrolo[2,3-b]pyrid-5-yl)-5-trimethylsilyl-1-[(3-methylphenyl)methyl]-1H-indole-2-carboxamide;
N-(1H-pyrrolo[2,3-b]pyrid-5-yl)-5-trifluoromethyl-1-[(3-methylphenyl)methyl]-1H-pyrrolo[2,3-b]pyridine-2-carboxamide;
N-(1H-pyrrolo[2,3-b]pyrid-5-yl)-6-trimethylsilyl-1-[(3-methyl phenyl)methyl]-1H-indole-2-carboxamide;
N-(1H-Pyrrolo[2,3-b]pyrid-5-yl)-5-trifluoromethyl-1-[[(3-trifluoromethyl)phenyl]methyl]-1H-indole-2-carboxamide;
N-(1H-Pyrrolo[2,3-b]pyrid-5-yl)-6-trifluoromethyl-1-[[(3-trifluoromethyl)phenyl]methyl]-1H-indole-2-carboxamide;
N-(1H-pyrrolo[2,3-b]pyrid-5-yl)-5-trifluoromethyl-1-[[(3-trifluoromethyl)phenyl]methyl]-1H-pyrrolo[2,3-b]pyridine-2-carboxamide;
N-(1H-Pyrrolo[2,3-b]pyrid-5-yl)-6-fluoro-1-[[(3-trifluoromethyl)phenyl]methyl]-1H-indole-2-carboxamide;
N-(1-Methyl-1H-pyrrolo[2,3-b]pyrid-5-yl)-5-fluoro-1-[(pyrid-4-yl)methyl)]-1H-indole-2-carboxamide;
N-(1-Methyl-1H-pyrrolo[2,3-b]pyrid-5-yl)-5-fluoro-1-[(pyrid-3-yl)methyl)]-1H-indole-2-carboxamide;
N-(1H-Pyrrolo[2,3-b]pyrid-5-yl)-5-trifluoromethyl-1-[(thiazol-2-yl)methyl]-1H-pyrrolo[2,3-b]pyridine-2-carboxamide;
N-(1H-Pyrrolo[2,3-b]pyrid-5-yl)-6-trimethylsilyl-1-[(thiazol-2-yl)methyl]-1H-indole-2-carboxamide;
N-(1H-Pyrrolo[2,3-b]pyrid-5-yl)-5-trifluoromethyl-1-[(thiazol-2-yl)methyl]-1H-indole-2-carboxamide;
N-(1H-Pyrrolo[2,3-b]pyrid-5-yl)-6-trifluoromethyl-1-[(thiazol-2-yl)methyl]-1H-indole-2-carboxamide;
N-(1H-Pyrrolo[2,3-b]pyrid-5-yl)-5-trimethylsilyl-1-[(thiazol-2-yl)methyl]-1H-indole-2-carboxamide;
N-(1H-Pyrrolo[2,3-b]pyrid-5-yl)-6-fluoro-1-[(thiazol-2-yl)methyl]-1H-indole-2-carboxamide;
N-(1H-Pyrrolo[2,3-b]pyrid-5-yl)-5-trifluoromethyl-1-[(pyrid-4-yl)methyl)]-1H-indole-2-carboxamide;
N-(1H-Pyrrolo[2,3-b]pyrid-5-yl)-6-trifluoromethyl-1-[(pyrid-4-yl)methyl)]-1H-indole-2-carboxamide;
N-(1H-Pyrrolo[2,3-b]pyrid-5-yl)-6-trimethylsilyl-1-[(pyrid-4-yl)methyl)]-1H-indole-2-carboxamide;
N-(1H-Pyrrolo[2,3-b]pyrid-5-yl)-5-trimethylsilyl-1-[(pyrid-4-yl)methyl)]-1H-indole-2-carboxamide;
N-(1H-Pyrrolo[2,3-b]pyrid-5-yl)-6-fluoro-1-[(pyrid-4-yl)methyl)]-1H-indole-2-carboxamide;
N-(1H-Pyrrolo[2,3-b]pyrid-5-yl)-5-trifluoromethyl-1-[(pyrid-4-yl)methyl)]-1H-pyrrolo[2,3-b]pyridine-2-carboxamide;
N-(2-Oxo-2,3-dihydro-1H-pyrrolo[2,3-b]pyrid-5-yl)-5-fluoro-1-[(3-fluorophenyl)methyl]-1H-indole-2-carboxamide;
N-(1H-Pyrrolo[2,3-b]pyrid-5-yl)-5-trifluoromethyl-1-[(3-fluorophenyl)methyl]-1H-indole-2-carboxamide;
N-(1-Methyl-1H-pyrrolo[2,3-b]pyrid-5-yl)-1-[(3-fluorophenyl)methyl]-1H-pyrrolo[2,3-c]pyridine-2-carboxamide;
N-(1H-Pyrrolo[2,3-b]pyrid-5-yl)-1-[(3-fluorophenyl)methyl]-1H-pyrrolo[2,3-c]pyridine-2-carboxamide;
N-(1H-Pyrrolo[2,3-b]pyrid-5-yl)-5-fluoro-1-[(pyrid-4-yl)methyl)]-1H-indole-2-carboxamide; and
N-(1-Methyl-1H-Pyrrolo[2,3-b]pyrid-5-yl)-5-trifluoromethyl-1-[(pyrid-4-yl)methyl)]-1H-indole-2-carboxamide;
or an acid-addition salt thereof.

12. A pharmaceutical composition comprising a compound of formula (I) according to claim 1, or a pharmaceutically acceptable salt thereof; in combination with at least one pharmaceutically acceptable excipient.

13. A pharmaceutical composition comprising a compound of formula (I) according to claim 8, or a pharmaceutically acceptable salt thereof; in combination with at least one pharmaceutically acceptable excipient.

14. A pharmaceutical composition comprising a compound of formula (I) according to claim 11, or a pharmaceutically acceptable salt thereof; in combination with at least one pharmaceutically acceptable excipient.

* * * * *

UNITED STATES PATENT AND TRADEMARK OFFICE
CERTIFICATE OF CORRECTION

PATENT NO.        : 8,354,425 B2
APPLICATION NO.   : 12/840659
DATED             : January 15, 2013
INVENTOR(S)       : Laurent Dubois et al.

Page 1 of 1

It is certified that error appears in the above-identified patent and that said Letters Patent is hereby corrected as shown below:

In the Specifications:

In column 36, line 48, delete "Methyl pyrrolo" and insert -- Methylpyrrolo --, therefor.

In column 37, line 11, delete "pyri d" and insert -- pyrid --, therefor.

In column 37, line 29, delete "methyl phenyl)" and insert -- methylphenyl) --, therefor.

In column 47-48, in Table 2, line 12, delete "CH, C–CF$_3$, CH, CH" and insert
-- CH, CH, C–CF$_3$, CH --, therefor.

In the Claims:

In column 56, line 56, in claim 4, delete "alkyl)$_3$," and insert -- alkyl)$_3$; --, therefor.

In column 59, line 59, in claim 11, delete "methyl phenyl)" and insert -- methylphenyl) --, therefor.

Signed and Sealed this
Thirtieth Day of April, 2013

Teresa Stanek Rea
*Acting Director of the United States Patent and Trademark Office*